United States Patent
Savarino

(10) Patent No.: US 10,017,547 B2
(45) Date of Patent: *Jul. 10, 2018

(54) **ADHESIN AS IMMUNOGEN AGAINST ENTEROTOXIGENIC *ESCHERICHIA COLI***

(71) Applicant: Naval Medical Research Center, Silver Spring, MD (US)

(72) Inventor: Stephen J. Savarino, Kensington, MD (US)

(73) Assignee: Naval Medical Research Center, Silver Spring, MD (US)

( * ) Notice: Subject to any disclaimer, the term of this patent is extended or adjusted under 35 U.S.C. 154(b) by 17 days.

This patent is subject to a terminal disclaimer.

(21) Appl. No.: 14/733,421

(22) Filed: Jun. 8, 2015

(65) Prior Publication Data

US 2015/0266932 A1 Sep. 24, 2015

Related U.S. Application Data

(63) Continuation of application No. 11/340,003, filed on Jan. 10, 2006, now Pat. No. 9,079,945.

(60) Provisional application No. 60/642,771, filed on Jan. 11, 2005.

(51) Int. Cl.
| | |
|---|---|
| *A61K 39/00* | (2006.01) |
| *A61K 39/385* | (2006.01) |
| *A61K 39/108* | (2006.01) |
| *A61K 39/02* | (2006.01) |
| *A61K 38/00* | (2006.01) |
| *C07K 2/00* | (2006.01) |
| *C07K 4/00* | (2006.01) |
| *C07K 5/00* | (2006.01) |
| *C07K 14/00* | (2006.01) |
| *C07K 16/00* | (2006.01) |
| *C07K 17/00* | (2006.01) |
| *C12P 21/04* | (2006.01) |
| *C07K 14/245* | (2006.01) |
| *C07K 16/12* | (2006.01) |

(52) U.S. Cl.
CPC ........ *C07K 14/245* (2013.01); *A61K 39/0258* (2013.01); *C07K 16/1232* (2013.01); *A61K 38/00* (2013.01); *A61K 2039/523* (2013.01); *A61K 2039/545* (2013.01); *C07K 2317/55* (2013.01); *C07K 2319/00* (2013.01); *C07K 2319/35* (2013.01)

(58) Field of Classification Search
CPC .. C07K 2319/00; C07K 14/245; A61K 38/00; A61K 39/0258
See application file for complete search history.

(56) References Cited

U.S. PATENT DOCUMENTS

| | | | |
|---|---|---|---|
| 6,906,736 B2 | 6/2005 | Altboum et al. | |
| 9,079,945 B2* | 7/2015 | Savarino | ........... A61K 39/0258 |
| 9,107,866 B2* | 8/2015 | Savarino | ........... A61K 39/0258 |
| 2002/0086037 A1 | 7/2002 | Hultgren et al. | |
| 2002/0150587 A1 | 10/2002 | Langermann et al. | |
| 2003/0099665 A1 | 5/2003 | Langermann et al. | |
| 2003/0138449 A1 | 7/2003 | Langermann et al. | |
| 2003/0199071 A1 | 10/2003 | Langermann et al. | |
| 2005/0054075 A1 | 3/2005 | Turner et al. | |
| 2005/0241024 A1 | 10/2005 | Langridge et al. | |
| 2006/0269560 A1 | 11/2006 | Savarino | |
| 2007/0237791 A1 | 10/2007 | Ranallo et al. | |

FOREIGN PATENT DOCUMENTS

| | | |
|---|---|---|
| WO | WO 2001/004148 | 1/2001 |
| WO | WO 2002/059156 | 8/2002 |
| WO | WO 2002/064162 | 8/2002 |
| WO | WO 2005/113827 | 12/2005 |

OTHER PUBLICATIONS

Bowie et al. (Science, 1990, 257:1306-1310).*
Ahren and Svennerholm (1982), "Synergistic protective effect of antibodies against *Escherichia coli* enterotoxin and colonization factor antigens." Infect. Immun. 38:74-79.
Altboum et al. (2003), "Genetic characterization and immunogenicity of coli surface antigen 4 from enterotoxigenic *Escherichia coli* when it is expressed in a Shigella live-vector strain." Infect. Immun. 71:1352-1360.
Anantha et al. (2004), "Evolutionary and functional relationships of colonization factor antigen I and other class 5 adhesive fimbriae of enterotoxigenic *Escherichia coli.*" Inf and Imm. 72: 7190-7201.
Barry et al. (2003), "Immune responses elicited against multiple enterotoxigenic *Escherichia coli* fimbriae and mutant LT expressed in attenuated Shigella vaccine strains." Vaccine 17: 333-340.
Bendtsen et al. (2004), "Improved prediction of signal peptides: SignalP 3.0." J Mol Biol 340:783-95.
Black (1990), "Epidemiology of travelers' diarrhea and relative importance of various pathogens." Rev Infect Dis 12 (Suppl 1):S73-S79.
Buhler et al. (1991), "Analysis of colonization factor antigen I, an adhesin of enterotoxigenic *Escherichia coli* 078: H11: fimbrial morphology and location of the receptor-binding site." Infect Immun 59:3876-3882.

(Continued)

*Primary Examiner* — Gary B Nickol
*Assistant Examiner* — Lakia J Jackson-Tongue
(74) *Attorney, Agent, or Firm* — McDonnell Boehnen Hulbert & Berghoff LLP

(57) ABSTRACT

The inventive subject matter relates to the methods for the induction of immunity and prevention of diarrhea resulting from *Escherichia coli*. The inventive subject matter also relates to the use *Escherichia coli* adhesins as immunogens and to the construction of conformationally stability and protease resistant *Escherichia coli* adhesin constructs useful for inducing immunity to *Escherichia coli* pathogenic bacteria. The methods provide for the induction of B-cell mediated immunity and for the induction of antibody capable of inhibiting the adherence and colonization of *Escherichia coli*, including enterotoxigenic *Escherichia coli*, to human cells.

39 Claims, 12 Drawing Sheets

(56) References Cited

OTHER PUBLICATIONS

Byrd et al. (2003), "Mucosal immunization of BALB/c mice using enterotoxigenic *Escherichia coli* colonization factors CFA/I and CS6 administered with and without a mutant heat-labile enterotoxin." Vaccine 21: 1884-93.
Choudhury et al. (1999), "X-ray structure of the FimC-FimH chaperone-adhesin complex from uropathogenic *Escherichia coli*." Science 285:1061-6.
Clemens et al. (1988), "Cross-protection by B subunit whole cell cholera vaccine against diarrhea associated with heat-labile toxin producing enterotoxigenic *Escherichia coli*: results of a large-scale field trial." J. Infect. Dis. 158: 372-377.
Cravioto et al. (1982), "Hemagglutination activity and colonization factor antigens I and II in enterotoxigenic and non enterotoxigenic *Escherichia coli* isolated from humans." Infect Immun 36:189-197.
Darfeuille-Michaud et al. (1990), "Adhesion of enterotoxigenic *Escherichia coli* to the human colon carcinoma cell line Caco-2 in culture." Infect Immun 58:893-902.
Dertzbaugh and Cox (1998), "The affinity of cholera toxin for Ni2+ ion." Protein Eng. 11: 577-581.
Domenighini et al. (1995), "Identification of errors among database sequence entries and comparison of correct amino acid sequences for the heat-labile enterotoxins of *Escherichia coli* and *Vibrio cholerae*." Mol. Microbiol 15: 1165-1167, (MicroCorrespondence).
Evans et al. (1975), "Plasmid-controlled colonization factor associated with virulence in *Esherichia coli* enterotoxigenic for humans." Infect Immun 12:656-667.
Evans et al. (1978), "Detection and characterization of colonization factor of enterotoxigenic *Escherichia coil* isolated from adults with diarrhea." Infect Immun 19:727-736.
Froehlich et al. (1994), "CooC and CooD are required for assembly of CS1 pili." Mol Microbiol 12:387-401.
Froehlich et al. (1995), "Genes for CS2 pili of enterotoxigenic *Escherichia coil* and their interchangeability with those for CS1 pili." Infect Immun 63:4849-56.
Gaastra and Svennerholm (1996), "Colonization factors of human enterotoxigenic *Escherichia coli* (ETEC)." Trends Microbiol 4:444-452.
Gaastra et al. (2002), "Antigenic variation within the subunit protein of members of the colonization factor antigen I group of fimbrial proteins in human enterotoxigenic *Escherichia coli*." Int J Med Microbiol 292:43-50.
Grewal et al. (1997), "A new putative fimbrial colonization factor, CS 19, of human enterotoxigenic *Escherichia coli*." Infect Immun 65:507-513.
Hall et al. (1989), "Purification and analysis of colonization factor antigen I, *coli* surface antigen 1, and *coli* surface antigen 3 fimbriae from enterotoxigenic *Escherichia coil*." J Bacteriol 171:6372-6374.
Hess et al. (2002), "Identification and characterization of hydrophobic *Escherichia coil* virulence proteins by liquid chromatography-electrospray ionization mass spectrometry." Anal Biochem 302:123-130.
Hirst (1999), "Cholera toxin and *Escherichia coli* heat-labile enterotoxin," in E. Alouf and J. H. Freer (ed.), The Comprehensive Sourcebook of Bacterial Protein Toxins, 2 ed, vol. 6. Academic Press, San Diego, p. 104-129.
Holmes (1997), "Heat-labile enterotoxins (*Escherichia coli*)," in R. Rappuloi and C. Montecucco (ed.), Guidebook to Protein Toxins and Their use in Cell Biology. Oxford University Press, New York, p. 30-33.
Holmgren and Czerkinsky (2005), "Muscosal immunity and vaccines." Nat. Med. 11: S45-53.
Huilan et al. (1991), "Etiology of acute diarrhoea among children in developing countries: a multicentre study in five countries." Bull World Health Organ 69:549-55.
Hung et al. (1996), "Molecular basis of two subfamilies of immunoglobulin-like chaperones." EMBO J. 15:3792-3805.
International Search Report from International Application No. PCT/US2006/000660, International Publication No. WO 2006/076285, dated Jul. 25, 2008.
International Search Report from International Application No. PCT/US2007/000712, International Publication No. WO 2007/114878, dated Oct. 14, 2008.
Jalajalcumari et al. (1989), "Genes for biosysnthesis and assembly of CS3 pili of CFA/II enterotoigenic *Escherichia coli*: novel regulation of pilus production by bypassing an amber codon." Mol. Micro 3:1685-1695.
Jobling and Holmes (2005), "Activation of second messenger pathways by ADP-ribosylation of G-proteins," in T. Proft (ed.), Microbial Toxins: Molecular and Cellular Biology, Horizon Bioscience, Wymondharn, United Kingdom, p. 9-46.
Jordi et al. (1992), "The complete nucleotide sequence of region 1 of the CFA/I fimbrial operon of human enterotoxigenic *Escherichia coli*." DNA Seq 2:257-263.
Khalil et al. (1999), "Characterization of an enterotoxigenic *Escherichia coli* strain from Africa expressing a putative colonization factor." Infect Immun 67:4019-4026.
Khalil, Cassels, Shaheen, Pannell, Kamal, Pittner, Mansour, Frenck, Savarino, and Peruski (2000), Presented at the 100th General Meeting of the American Society for Microbiology, Los Angeles, CA, Abstract B-79.
Kuehn et al. (1992), "P pili in uropathogenic *E. coli* are composite fibres with distinct fibrillar adhesive tips." Nature 356:252-5.
Lee et al. (2004), "Plant-synthesized *E. coli* CFA/I fimbrial protein protects Caco-2 cells from bacterial attachment." Vaccine 23(2): 222-31.
Levine et al. (1984), "Prevention of enterotoxigenic *Escherichia coli* diarrheal infection in man by vaccines that stimulate anti-adhesion (anti-pili) immunity," In E.C. Boedeker (ed.), Attachment of Micro-organisms to the Gastrointestinal Mucosal Surface. CRC Press, Boca Raton, p. 223-244.
Li et al. (2004), "Use of translational fusion of the MrpH fimbrial adhesin-binding domain with the cholera toxin A2 domain, coexpressed with the cholera toxin B subunit, as an intranasal vaccine to prevent experimental urinary tract infection by *Proteus mirabilis*." Infect. Immun. 72: 7306-7310.
Low et al. (1996), "Fimbriae," In *Escherichia coli* and *Salmonella*: Cellular and Molecular Biology (Neidhardt et al. eds.), 2nd ed, vol. 1, ASM Press, Washington DC, pp. 146-157.
Nataro and Kaper (1998), "Diarrheagenic *Escherichia coli*." Clin Microbiol Rev 11:142-201.
Peltola et al. (1991), "Prevention of traveller's diarrhoea by oral B-subunit/whole-cell cholera vaccine." Lancet 338: 1285-1289.
Perez-Casal et al. (1990), "Gene encoding the major subunit of CS1 pili of human enterotoxigenic *Escherichia coli*." Infect Immun 58:3594-3600.
Perler (2002), "InBase, the Intein Database." Nuc. Acids. Res. 30:383-384.
Poole et al. (2007), "Donor strand complementation governs intersubunit interaction of fimbriae of the alternate chaperone pathway." Molecular Microbiology 63(5): 1372-84.
Qadri et al. (2005), "Enterotoxigenic *Escherichia coli* in developing countries: Epidemiology, microbiology, clinical features, treatment, and prevention." Clin. Microbiol. Rev 18: 465-483.
Ramer et al. (2002), "The Type IV pilus assembly complex: Biogenic interactions among the bundle forming pilus proteins of enteropathogenic *Escherichia coli*." J Bacteriol 184:3457-65.
Rao et al. (2003), "High disease burden due to enterotoxigenic *Escherichia coli* diarrhea in early life among rural Egyptian children." J Clin Microbiol 41:4862-4864.
Rao et al. (2005), "Serologic correlates of protection against enterotoxigenic *Escherichia coli* diarrhea." J. Infect. Dis. 191:562-570.
Sakellaris et al. (1996), "Assembly proteins of CS1 pili of enterotoxigenic *Escherichia coli*." Mol. Microbiol. 21:529-41.
Sakellaris and Scott (1998), "New tools in an old trade: CS1 pilus morphogenesis." Mol Microbiol 30:681-7.
Sakellaris et al. (1999), "A conserved residue in the tip proteins of CS1 and CFA/I pili of enterotoxigenic *Escherichia coli* that is essential for adherence." Proc Natl Acad Sci, USA 96:12828-12832.
Sakellaris et al. (1999), "The level of expression of the minor pilin subunit, CooD, determines the number of CS1 pili assembled on the cell surface of *Escherichia coli*." J Bacteriol 181:1694-7.

(56) References Cited

OTHER PUBLICATIONS

Sauer et al. (1999), Structural basis of chaperone function and pilus biogenesis. Science 285:1058-61.
Savarino et al. (1999), "Oral, inactivated, whole cell enterotoxigenic *Escherichia coli* plus cholera toxin B subunit vaccine: results of the initial evaluation in children. PRIDE Study Group." J. Infect. Dis. 179: 107-114.
Savarino, S.J., R. Abu-Elyazeed, M.R. Rao, R.W. Frenck, I. Abdel-Messih, H.E.R., S. Putnam, H. El-Mohamady, T. Wierzba, B. Pittner, K. Kamal, P. Moyer, M.B.Z., A.M. Svennerholm, Y.J. Lee, and J.D. Clemens (2003), Presented at the Sixth Annual Conference on Vaccine Research, Arlington, VA, Abstract S11.
Schulz et al. (1997), "Disruption of the guanylyl cyclase-C gene leads to a paradoxical phenotype of viable but heat-stable enterotoxin-resistant mice." J. Clin. Invest. 100: 1590-1595.
Scott et al. (1992), "CooB is required for assembly but not transport of CS1 pilin." Mol Microbiol 6:293-300.
Smyth et al. (1996), "Fimbrial adhesins: similarities and variations in structure and biogenesis." FEMS Immunology and Medical Microbiology 16(2): 127-39.
Soto and Hultgren (1999), "Bacterial adhesins: common themes and variations in architecture and assembly." J Bacteriol 181:1059-1071.
Spangler (1992), "Structure and function of cholera toxin and the related *Escherichia coli* heat-labile enterotoxin." Microbiol. Rev. 56: 622-647.
Supplementary European Search Report from European Application No. EP 06717818, dated Jul. 31, 2009, 1 page communication.
Supplementary European Search Report from European Application No. EP 07748881, dated Dec. 28, 2009, 7 pages.
Svennerholm et al. (1997), "Oral inactivated vaccines against enterotoxigenic *Escherichia coli,*" In Levine et al. (ed.), New Generation Vaccines, II ed. Marcel Dekker, Inc., New York, p. 865-874.
Tinker et al. (2005), "Characterization of fluorescent chimeras of cholera toxin and *Escherichia coli* heat-labile enterotoxins produced by use of the twin arginine translocation system." Infect. Immun. 73: 3627-3635.
Turner et al. (2001), "Construction and characterization of genetically defined aro omp mutants of enterotoxigenic *Escherichia coli* and preliminary studies of safety and immunogencity in humans." Infect. Immun. 69: 4969-4979.
Viboud et al. (1996), "Binding of enterotoxigenic Escherichia coli expressing different colonization factors to tissue-cultured Caco-2 cells and to isolated human enterocytes." Microb Pathogen 21:139-147.
Yu et al. (2001), "Assembly of cholera toxin-antigen fusion proteins in transgenic potato." Transgenics 3: 153-62.

Zavialov et al. (2003), "Structure and biogenesis of the capsular FI antigen from Yersinia pestis: preserved folding energy drives fiber formation." Cell 113:587-596.
Qadri, et al., "Safety and immunogenicity of an oral, inactivated enterotoxigenic *Escherichia coli* plus cholera toxin B subunit vaccine in Bangladeshi children 18-36 months of age," Vaccine 21, p. 2394-2403 (2003).
European Search Report regarding EP Application No. 0671 7818 dated Apr. 9, 2009.
Holderness, "Identification of immunodominant T cell epitopes from enterotoxigenic *E. coli* colonization factor antigen I (CFA/I) responsible for T helper cell cytokines." Thesis submitted at Montana State University, Bozeman, Montana (Apr. 2012), 111 pages, (thesis).
Savarino, et al., "Efficacy of an Oral, Inactivated Whole-Cell Enterotoxigenic *E. coli*/Cholera Toxin B Subunit Vaccine in Egyptian Infants," Sixth Annual Conference on Vaccine Research, Arlington, VA, p. 48 (2003) Abstract S11.
Barnhart, et al., "PapD-like chaperones provide the missing information for folding of pilin proteins." (2002) Proc. Natl. Acad. Sci. USA, 97(14):7709-14.
Krasan, et al., Evidence for donor strand complementation in the biogenesis of Haemophilus influenzae haemagglutinating pili. (2000). Mol. Micobiology 35(6):1335-47.
Zavialov, et al., "Donor strand complementation mechanism in the biogenesis of non-pilus systems." (2002). Mol. Micro. 45(4):983-95.
Verdonck, et al., "Conserved regions in the sequence of the F4 (K88) fimbrial adhesin FaeG suggest a donor strand mechanism in F4 assembly." (2004). Vet. Micro 102:215-225.
Anderson, et al., "An atomic resolution model for assembly architecture and function of the Dr adhesins." (2004). Mol. Cell 15:647-57.
Khandelwal, et al., "Insecticidal pilin subunit from the insect pathogen Xenorhabdus nematophila." (2004). J. Bact. 186:6465-6476.
Normark, "Anfinsen comes out of the cage during assembly of the bacterial pilus." (2000). Proc. Natl. Acad. Sci. USA 97(14):7670-7672.
(No. Author Given), International research sheds light on *Escherichia coli,* (Published Wednesday, Sep. 1, 2004) Medical Research News, http://www.news-medical.net, Led by senior auther Dr. Stephen Matthews
Yakhchali, et al., "Epitope analysis of the CS3 fimbrial subunit of human enterotoxigenic *Escherichia coli* and the construction of novel CS3::ST and CS3::LT-B immunogens." (1997). Behring Inst Mitt. 98:124-134.
Richardson et al., "Incidence of the cblA major subunit pilin gene amongst *Burkholderia* species." (2001). FEMS Microbiology Letters 196:61-66.

\* cited by examiner

|  |  | Major subunit | Fimbriae |
|---|---|---|---|
| ▓▓N▓T▓S▓▓V▓▓QA | (SEQ ID NO: 7) | CfaB | CFA/I |
| ▓▓T▓T▓S▓▓T▓▓QA | (SEQ ID NO: 8) | CsfA | CS4 |
| ▓▓N▓T▓S▓▓T▓▓QA | (SEQ ID NO: 9) | CsuA1 | CS14 |
| ▓▓N▓T▓S▓▓T▓▓QA | (SEQ ID NO: 10) | CsuA2 | CS14 |
| ▓▓T▓T▓S▓▓I▓▓QS | (SEQ ID NO: 11) | CooA | CS1 |
| ▓▓T▓T▓S▓▓T▓▓QS | (SEQ ID NO: 15) | CosA | PCFO71 |
| ▓▓N▓T▓R▓S▓▓K▓▓QA | (SEQ ID NO: 13) | CsbA | CS17 |
| ▓▓N▓T▓R▓S▓▓K▓▓QA | (SEQ ID NO: 12) | CsdA | CS19 |
| ▓▓N▓T▓T▓S▓▓T▓▓QS | (SEQ ID NO: 14) | CotA | CS2 |
| ▓▓D▓T▓T▓N▓▓TT▓▓SA | (SEQ ID NO: 24) | CblA | Bcep |
| ▓▓D▓T▓T▓N▓ST▓▓QA | (SEQ ID NO: 25) | TsaB | Styp |
| UZKxUTUxAxUDxxUDUUxx | (SEQ ID NO: 26) |  |  |

FIG 4

ADHESIN AS IMMUNOGEN AGAINST ENTEROTOXIGENIC *ESCHERICHIA COLI*

CROSS-REFERENCES TO RELATED APPLICATIONS

This application is a continuation of U.S. application Ser. No. 11/340,003, filed Jan. 10, 2006, (issued as U.S. Pat. No. 9,079,945), which claims priority to U.S. Provisional Application No. 60/642,771, filed Jan. 11, 2005, the contents of each of which are hereby incorporated by reference.

BACKGROUND OF INVENTION

Field of the Invention

The inventive subject matter relates to a method of inducing an immune response against diarrheagenic bacteria including enterotoxigenic *Escherichia coli* using bacterial fimbriae or fibrillar components. The method contemplates using *Escherichia coli* adhesins as immunogens against diarrheagenic bacteria.

Description of Related Art

Enterotoxigenic *Escherichia coli* (ETEC) are a principal cause of diarrhea in young children in resource-limited countries and also travelers to these areas (1, 2). ETEC produce disease by adherence to small intestinal epithelial cells and expression of a heat-labile (LT) and/or heat-stable (ST) enterotoxin (3). ETEC typically attach to host cells via filamentous bacterial surface structures known as colonization factors (CFs). More than 20 different CFs have been described, a minority of which have been unequivocally incriminated in pathogenesis (4).

Firm evidence for a pathogenic role exists for colonization factor antigen I (CFA/I), the first human-specific ETEC CF to be described. CFA/I is the archetype of a family of eight ETEC fimbriae that share genetic and biochemical features (5, 4, 6, 7). This family includes *coli* surface antigen 1 (CS1), CS2, CS4, CS14, CS17, CS19 and putative colonization factor 071 (PCFO71). The complete DNA sequences of the gene clusters encoding CFA/I, CS1 and CS2 have been published (8, 9, 10, 11, 12). The genes for the major subunit of two of the other related fimbriae have been reported (13, 6). The four-gene bioassembly operons of CFA/I, CS1, and CS2 are similarly organized, encoding (in order) a periplasmic chaperone, major fimbrial subunit, outer membrane usher protein, and minor fimbrial subunit. CFA/I assembly takes place through the alternate chaperone pathway, distinct from the classic chaperone-usher pathway of type I fimbrial formation and that of other filamentous structures such as type IV pili (14, 15). Based on the primary sequence of the major fimbrial subunit, CFA/I and related fimbriae have been grouped as class 5 fimbriae (16).

Similar, but distinct from class 5 fimbriae, *coli* surface antigen 3 (CS3) represents the common adhesive fibrilla of the ETEC colonization factor antigen II (CFA/II) complex. ETEC expressing these antigens are prevalent in many parts of the world. Although the conformational nature of CS3 containing fibrillae are even less understood than class 5 fimbriae, it is anticipated that these structures will also be important components in contemplated anti-ETEC vaccines.

Studies of CS1 have yielded details on the composition and functional features of Class 5 fimbriae (17). The CS1 fimbrial stalk consists of repeating CooA major subunits. The CooD minor subunit is allegedly localized to the fimbrial tip, comprises an extremely small proportion of the fimbrial mass, and is required for initiation of fimbrial formation (18). Contrary to earlier evidence suggesting that the major subunit mediates binding (19), recent findings have implicated the minor subunit as the adhesin and identified specific amino acid residues required for in vitro adhesion of CS1 and CFA/I fimbriae (20). The inferred primary amino acid structure of those major subunits that have been sequenced share extensive similarity. Serologic cross-reactivity of native fimbriae is, however, limited, and the pattern of cross-reactivity correlates with phylogenetically defined subtaxons of the major subunits (13).

Implication of the minor subunits of Class 5 fimbriae as the actual adhesins entreats scrutiny regarding the degree of their conservation relative to that of the major subunits. It was speculated that CooD and its homologs retained greater similarity due to functional constraints imposed by ligand binding requirements and/or its immunorecessiveness, itself attributable to the extremely large ratio of major to minor subunits in terms of fimbrial composition. Studies were conducted to examine the evolutionary relationships of the minor and major subunits of Class 5 ETEC fimbriae as well as the two assembly proteins (21). It was demonstrated that evolutionary distinctions exist between the Class 5 major and minor fimbrial subunits and that the minor subunits function as adhesins. These findings provide practical implications for vaccine-related research.

The nucleotide sequence of the gene clusters that encode CS4, CS14, CS17, CS19 and PCFO71 was determined from wild type diarrhea-associated isolates of ETEC that tested positive for each respective fimbriae by monoclonal antibody-based detection (21). The major subunit alleles of the newly sequenced CS4, CS14, CS17 and CS19 gene clusters each showed 99-100% nucleotide sequence identity with corresponding gene sequence(s) previously deposited in GenBank, with no more than four nucleotide differences per allele. Each locus had four open reading frames that encoded proteins with homology to the CFA/I class chaperones, major subunits, ushers and minor subunits. As previously reported (13), the one exception was for the CS14 gene cluster, which contained two tandem open reading frames downstream of the chaperone gene. Their predicted protein sequences share 94% amino acid identity with one another and are both homologous to other Class 5 fimbriae major subunits.

Examination of the inferred amino acid sequences of all the protein homologs involved in Class 5 fimbrial biogenesis reveals many basic similarities. Across genera, each set of homologs generally share similar physicochemical properties in terms of polypeptide length, mass, and theoretical isoelectric point. All of the involved proteins contain an amino-terminal signal peptide that facilitates translocation to the periplasm via the type II secretion pathway. None of the major subunit proteins contain any cysteine residues, while the number and location of six cysteine residues are conserved for all of the minor subunits except that of the *Y. pestis* homolog 3802, which contains only four of these six residues.

Type 1 and P fimbriae have been useful models in elucidating the genetic and structural details of fimbriae assembled by the classical chaperone-usher pathway (23, 24, 25). An outcome of this work has been development of the transformative principle of donor strand complementation, a process in which fimbrial subunits non-covalently interlock with adjoining subunits by iterative intersubunit sharing of a critical, missing β-strand (22, 26). Evidence has implicated this same mechanism in the folding and quaternary conformational integrity of *Haemophilus influenzae* hemagglutinating pili (27), and *Yersinia pestis* capsular protein, a non-fimbrial protein polymer (28). Both of 100 these structures are distant Class I relatives of Type 1 and P fimbriae that are assembled by the classical chaperone-usher pathway. From an evolutionary perspective, this suggests that the mechanism of donor strand complementation arose in a primordial fimbrial system from which existing fimbriae of this Class have derived. While donor strand complementation represents a clever biologic solution to the problem of protein folding for noncovalently linked, polymeric surface proteins, its exploitation by adhesive fimbriae other than those of the classical usher-chaperone pathway has not been demonstrated.

Common to fimbriae assembled by the alternate chaperone pathway and the classical chaperone-usher pathway are the requirement for a periplasmic chaperone to preclude subunit misfolding and an usher protein that choreographs polymerization at the outer membrane. That the fimbrial assembly and structural components of these distinct pathways share no sequence similarity indicates that they have arisen through convergent evolutionary paths. Nevertheless, computational analyses of the CFA/I structural subunits suggests the possibility that donor strand complementation may also govern chaperone-subunit and subunit-subunit interaction.

The eight ETEC Class 5 fimbriae clustered into three subclasses of three (CFA/I, CS4, and CS14), four (CS1, PCFO71, CS17 and CS19), and one (CS2) member(s) (referred to as subclasses 5a, 5b, and 5c, respectively) (21). Previous reports demonstrated that ETEC bearing CFA/I, CS2, CS4, CS14 and CS19 manifest adherence to cultured Caco-2 cells (6, 22). However, conflicting data have been published regarding which of the component subunits of CFA/I and CS1 mediate adherence (19, 20).

This question of which fimbrial components is responsible for mediating adherence was approached by assessing the adherence-inhibition activity of antibodies to intact CFA/I fimbriae, CfaB (major subunit), and to non-overlapping amino-terminal (residues 23-211) and carboxy-terminal (residues 212-360) halves of CfaE (minor subunit) in two different in vitro adherence models (21). It was demonstrated that the most important domain for CFA/I adherence resides in the amino-terminal half of the adhesin CfaE (21).

The studies briefly described above provide evidence that the minor subunits of CFA/I and other Class 5 fimbriae are the receptor binding moiety (20). Consistent with these observations, because of the low levels of sequence divergence of the minor subunits observed within fimbrial subclasses 5a and 5b (20), the evolutionary relationships correlated with cross-reactivity of antibodies against the amino-terminal half of minor subunits representing each of these two subclasses (21).

An aspect of this invention is a method of inducing an immune response against ETEC strains incorporating either or both of class 5 fimbriae or conformationally stable fimbriae components responsible for fimbriae adhesion or CS3 fibrillae or conformationally stable CS3 fibrillae components.

SUMMARY OF THE INVENTION

Currently available vaccines against many diarrheagenic bacteria such as enterotoxigenic *Escherichia coli* are not adequately efficacious. New vaccine formulations against these organisms are critical, especially for developing countries where diarrheal diseases are most prevalent and medical infrastructure is limited.

An object of the invention is a method of inducing an immune response, including antibody responses, against class 5 *Escherichia coli* fimbriae by administration of polypeptides encoding fimbrial adhesin or fibrillar adhesin.

A still further object is the prevention of colonization of *Escherichia coli* by inhibiting adherence of fimbriae or fibrillae to host cells.

An additional object is the construction of conformationally-stable and protease resistant adhesin polypeptide constructs for use in vaccine formulations.

A still additional object is the use of the adhesin polypeptide constructs to induce immunity to *Escherichia coli*, including enterotoxigenic *E. coli*, fimbriae.

These and other objects of the invention are accomplished by employing *Escherichia coli* adhesin polypeptides as an immunogenic component to induce immunity.

BRIEF DESCRIPTION OF THE DRAWINGS

FIG. 4. A highly conserved β-strand motif in the major structural subunits of Class 5 fimbriae. This is a multiple alignment of the amino-termini of the mature form of the major subunits, with consensus sequence shown below. This span is predicted to form an interrupted β-strand motif spanning residues 5-19 (demarcated by yellow arrows below consensus). Shading of conserved residues indicate class as follows: blue, hydrophobic; red, negatively charged residues; turquoise, positively charged residues; and green, proline. Abbreviations: Bcep, *Burkholderia cepacia*; Styp, *Salmonella typhi*. U, hydrophobic residue; x, any residue; Z, E or Q.

DETAILED DESCRIPTION OF PREFERRED EMBODIMENTS

Figure 1:
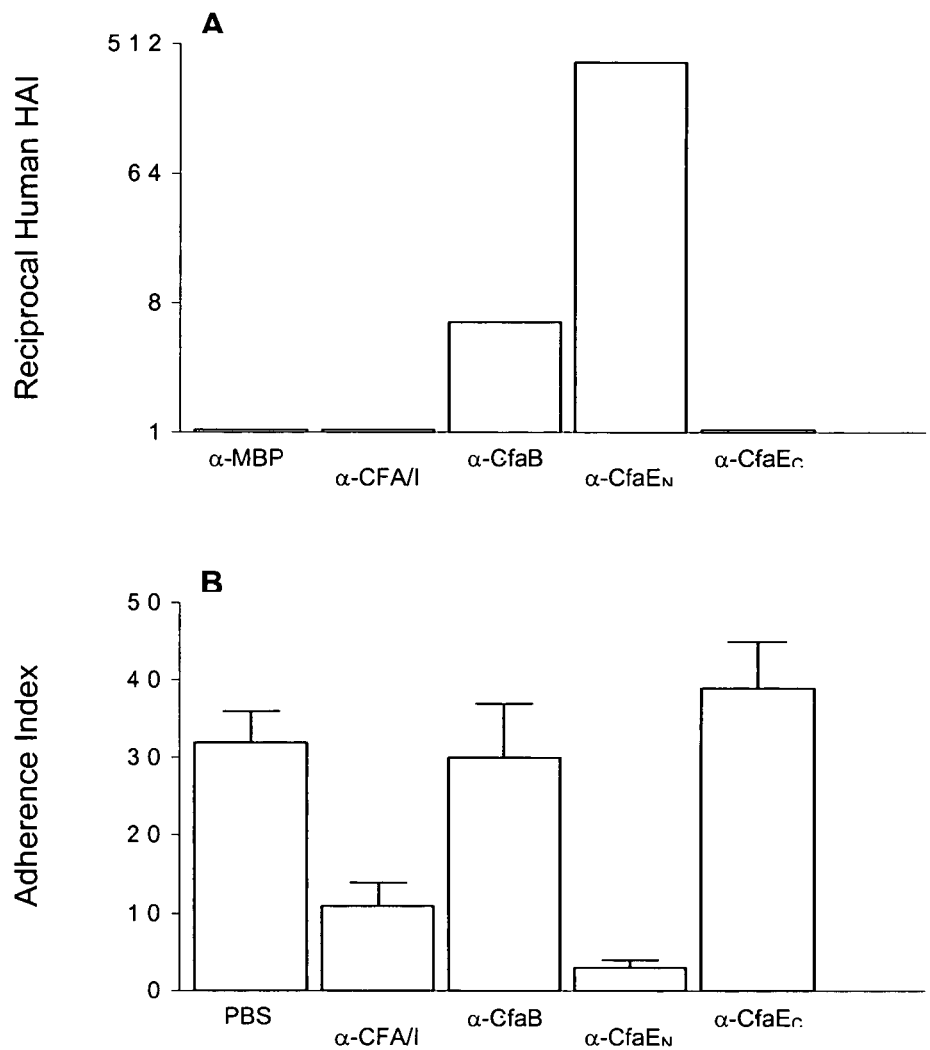
FIG. 1. Inhibitory effects of different $F_{ab}$ antibody preparations on adherence of strain H10407 (CFA/I) in two in vitro adherence models.

The present invention relates to methods and a biological composition for the induction of anti-adhesive immune responses by the administration of fimbriae or fimbrial adhesin components. I hereby state that the information recorded in computer readable form is identical to the written sequence listing.

Adhesin, the distal molecular component of enterotoxigenic *Escherichia coli* fimbriae, are the likely effectors for bacterial attachment to host cells (21). Therefore, adhesins are critical for bacterial colonization and pathogenicity.

The inventive method, immunization with adhesive subunits of class 5 fimbriae, will induce principally immunoglobulin mediated immunity, that specifically binds to bacterial adhesin to disrupt colonization of diarrheagenic bacteria. The method, therefore, will provide superior and more efficacious immunity against diarrheagenic bacteria. Furthermore, the use of fimbrial adhesin subunits in place of intact fimbriae or whole bacteria will likely require significantly less antigen to elicit immunity with improved efficacy of immunity.

The invention provides a method for inducing immunity by administration of polypeptides encoding *Escherichia coli* adhesin, which is the host-cell adhesive component structurally located at the tip of *Escherichia coli* fimbriae. The archetype fimbriae, colonization factor antigen I (CFA/I) is found on the most important enterotoxigenic *Escherichia coli* (ETEC) strains. However, because of the close evolutionary relationship of the ETEC adhesins, other class 5 fimbriae can also be utilized.

Conformational stability, and potentially protease resistance, of adhesin polypeptides is important to ensure maximum immunogenicity. Conformational integrity of adhesin monomers is conferred by a donated β-strand provided by an adjacent major structural fimbrial monomer. For example, conformational stability of the CFA/I adhesin, CfaE, is provided by the donor β-strand from CfaB.

For improved anti-fimbrial adhesin immunity, an aspect of the invention is conferral of conformational stability on adhesin polypeptide sequences. In order to ensure conformational stability of adhesin polypeptide immunogens with concomitant improved efficaciousness of vaccines, an aspect of this invention is polypeptide constructs designed to operatively provide a donor β-strand to adjacent adhesin polypeptide sequences. The constructs are composed of adhesin polypeptides linked at the C-terminal end to a linker polypeptide which is in turn linked, at the C-terminal end, to a polypeptide encoding all or a portion of a major fimbrial structural subunit, such as CfaB.

Example 1

Adhesin is the Most Important Vaccine-Related Enterotoxigenic *Escherichia coli* Bacterial Component Class 5 *Escherichia coli* Fimbriae Binding.

CFA/I is the archetype of a family of ETEC fimbriae sharing genetic and biochemical features (5, 4, 6, 7). The gene operons are composed of a periplasmic chaperone, major fimbrial subunit, outer membrane usher protein and a minor fimbrial subunit. Based on the major subunit sequence, CFA/I and related fimbriae have been grouped together as class 5 fimbriae (16, 21). Studies have confirmed that there is a confirmed functional distinction between class 5 major and minor fimbrial subunits and that the minor subunits serve as adhesins. Therefore, the minor subunits are the most important component of fimbriae for vaccine construction.

Type strains that individually express each of the Class 5 ETEC fimbriae were characterized with respect to erythrocyte adherence by mannose-resistant hemagglutination (MRHA) with type A human, bovine, and chicken erythrocytes (21). The phenotypes of all ETEC strains used in adhesion experiments are shown in Table 1. The type strains that expressed CS1, CS4, CS14, CS17, CS19 and PCFO71 were each isolated from the feces of young children with diarrhea, as part of a longitudinal study of childhood diarrhea in Egypt (29).

ETEC strains were tested for mannose-resistant hemagglutination (MRHA) of human type A, bovine, and chicken erythrocytes. MRHA methods were based on previously described procedures (30). The results shown are shown in Table 1.

In these studies, for routine propagation and protein expression, bacteria were grown in Luria-Bertani medium (31) or in rich medium (10 g tryptone, 5 g yeast extract, 5 g NaCl, and 2 g glucose per L). For hemagglutination and tissue culture adherence assays, cultures were grown on CFA agar (32) with or without addition of 1.5 g of Bacto Bile Salts no. 3 (Difco, Detroit, Mich.) per liter. Ampicillin (62.5 µg/ml) and kanamycin (50 µg/ml) were added as needed for selection pressure. Human erythrocytes were harvested as needed from a single volunteer donor, and bovine and chicken erythrocytes were purchased from Lampire Laboratories (Pipersville, Pa.). Erythrocytes were stored for up to two weeks at 4° C. in Alsever's solution prior to use. Just before each assay, erythrocytes were washed and suspended in PBS with 0.5% D-mannose to a final concentration of 3%. Bacteria were grown overnight at 37° C. and suspended in PBS with 0.5% D-mannose to a final concentration of about 1×10$^{10}$ colony forming units (cfu)/ml. Equal volumes (25 µl each) of 3% red cells, bacterial suspension, and PBS with 0.5% D-mannose were added and mixed in wells on a 12-well ceramic tile (CoorsTec, Golden, Colo.), rocked on ice for 20 min, graded by visual inspection, and scored as follows: negative, indicating no MRHA activity; 1+ indicating a low, weak reaction; 2+ denoting a moderate reaction; 3+ indicating a strong reaction; and 4+a nearly instantaneous and complete reaction involving all of the erythrocytes.

We also analyzed component subunit adherence to Caco-2 cells. The results of these studies are also shown in Table 1. Adherence assays were performed as described previously (33, 34) with minor modifications. Briefly, Caco-2 cells were maintained at 37° C. in air supplemented with 5% $CO_2$ in EMEM media (Minimum Essential Medium, Eagle's, in Earle's Balanced Salt Solution) supplemented with 2 mM L-glutamine, 20% fetal bovine serum, 0.1 M non-essential amino acids, 1 mM sodium pyruvate, and 1.5 g/liter sodium bicarbonate. Cells were seeded in 24 well plates (Costar, Corning, N.Y.) loaded with tissue culture-treated glass cover slips (Fisher Scientific), and incubated for 14 days (±1 d) to post-confluence, washed with PBS, and covered with 750 µl of the supplemented EMEM prior to the assay. Bacterial strains were grown on CFA agar with or without bile salts overnight at 37° C. and suspended to $1×10^9$ bacteria/ml in supplemented EMEM with 1% D-mannose. The suspension was added to the tissue culture wells at a final concentration of $2.5×10^8$ bacteria/ml. Plates were incubated, washed, fixed, stained and mounted as described (34), and observed microscopically. The number of bacteria adherent to 100 randomly selected cells was counted to give an average number of cells with at least 1 adherent bacteria (adherence index 1), and number of bacteria per Caco-2 cell with at least one adherent bacteria (adherence index 2). For each bacterial strain, a minimum of 3 experiments was done in duplicate to determine the adherence indices, expressed as the mean±standard deviation (SD).

It has previously been reported that ETEC bearing CFA/I, CS2, CS4, and CS14 and CS19 manifest adherence to cultured Caco-2 cells (6, 22). Caco-2 cell adherence assays on each of the ETEC type strains bearing the Class 5 fimbriae were performed to confirm these findings and quantify the level of adherence for each strain. The results (Table 1) indicated that indeed the strains bearing CFA/I, CS4, CS14 and CS2 each showed moderate to high level Caco-2 cell adherence, while a lower level of adherence was observed for the CS19-bearing strain. In contrast, the strains expressing CS1, CS17 and PCFO71 manifest marginal levels of adherence. Transformation of the strains bearing Subclass 5b fimbriae with a plasmid containing the CFA/I positive regulator cfaD was associated with an increase in Caco-2 cell adherence only for the CS19-ETEC strain WS0115A.

Considering the evolutionary relationships of the Class 5 ETEC fimbriae, it can be seen that there are some distinguishing functional characteristics that correlate with their phylogeny. Subclass 5a fimbriae are distinct from the others by virtue of their ability to cause MRHA of human type A erythrocytes. With the exception of the CS19-ETEC, Subclass 5b fimbriae show weak if any adherence to cultured Caco-2 cells, differentiating them from the other two subclasses.

TABLE 1

In vitro adherence phenotypes of ETEC type strains bearing CFA/I and related Class 5 fimbriae.

| Strain | CF type | MRHA | | | Caco-2 cell adherence[a] | |
| --- | --- | --- | --- | --- | --- | --- |
| | | human A | bovine | chicken | Index 1[b] | Index 2[c] |
| H10407 | CFA/I | 4+ | 4+ | 3+ | 54.3 ± 15.4 | 14.2 ± 2.7 |
| WS2560B | CS4 | 2+ | 2+ | 1+ | 26.7 ± 7.0 | 2.9 ± 1.6 |
| WS3294A | CS14 | 2+ | 3+ | 3+ | 63.3 ± 5.8 | 8.2 ± 2.4 |
| WS1974A | CS1 | — | 3+ | — | 12.7 ± 8.6 | 2.1 ± 1.1 |
| WS2173A | PCFO71 | — | 4+ | 2+ | 12.7 ± 6.2 | 1.8 ± 0.6 |
| WS6788A | CS17 | — | 4+ | — | 10.0 ± 2.6 | 1.1 ± 0.2 |
| WS0115A | CS19 | — | 4+ | 2+ | 19.3 ± 6.0 | 1.8 ± 0.8 |
| C91f | CS2 | — | 3+ | 3+ | 69.3 ± 4.7 | 15.1 ± 4.7 |

[a]Represents the mean of at least 3 experiments, each done in duplicate.
[b]Mean proportion of Caco-2 cells with at least one adherent bacteria (±SD)
[c]Mean number of adherent bacteria per Caco-2 cell with at least one adherent bacteria (±SD)

Adhesin are Responsible for Fimbriae Binding.

In order to determine the fimbriae components responsible for host cell binding the ability of specific antibody to adhesins to inhibit CFA/1 and CS1 fimbriae adherence was analyzed (21). We further evaluated the question whether antibody to these moieties would cross-react in accordance to evolutionary relationships. This was evaluated indirectly by measuring adherence-inhibition activity of antibodies to intact CFA/I fimbriae, CfaB (major subunit), and to non-overlapping amino-terminal (residues 23-211) and carboxy-terminal (residues 212-360) halves of CfaE (minor subunit) in two different in vitro adherence models (see SEQ ID No. 4 for sequence of CfaE).

CFA/I and CS17 fimbriae were purified as previously described (35, 36). Rabbit polyclonal antibody preparations were prepared against MBP-$CfaB_{24-170}$, MBP-$CfaE_{23-211}$, MBP-$CfaE_{212-360}$, MBP-$CsbD_{19-214}$, and against native CFA/I and CS17 fimbriae (21). Each of these above E. coli type strains described above, except for those that expressed CFA/I, CS1 and CS2, was also the source of DNA for sequence analysis of the corresponding fimbrial operon. E. coli BL21 (F⁻ ompT hsdSB(rB⁻ mB⁻) gal dcm) was obtained from a commercial source (New England Biolabs, Beverly, Mass.) and used for cloning and expression of maltose-binding protein (MBP) fusions. Rabbit immunizations and antiserum collection were performed by Harlan Bioproducts for Science, Inc. (Indianapolis, Ind.). Purified IgG was derived from each antiserum using Hi-Trap Protein G columns as directed by the manufacturer (Amersham Pharmacia, Piscataway, N.J.). From each of these preparations, $F_{ab}$ fragments were generated using the Pierce ImmunoPure $F_{ab}$ preparation kit (Pierce, Rockford, Ill.).

ETEC strains were tested for mannose-resistant hemagglutination (MRHA). For hemagglutination inhibition (HAI) assays, each bacterial strain was used at a concentration corresponding to two times the minimal hemagglutination titer (2×MHT). The MHT was determined at the start of each HAI assay day by making serial two-fold dilutions of the bacterial suspension (from a starting concentration of $1×10^{10}$ cfu/ml) in PBS. A total of 25 µl of each dilution was added to equal volumes of 3% erythrocyte suspension and PBS with 0.5% D-mannose and rocked on ice. The MHT was defined as the reciprocal of the lowest concentration of bacteria showing at least 1+ MRHA. To determine the HAI titer of each $F_{ab}$ antibody preparation, a two-fold dilution series was made starting with the stock antibody solution (2 mg/ml). A 25 µl volume of each $F_{ab}$ dilution was added to an equal volume of a 2×MHT bacterial suspension in the ceramic tile wells and pre-incubated at room temperature with rocking for 20 min. An equal volume of erythrocyte suspension (3%) was then added to each well, the tiles were rocked on ice for 20 min, and MRHA was scored as above. The HAI titer was expressed as the reciprocal of the highest dilution of antiserum that completely inhibited MRHA.

For Caco-2 cell adherence inhibition experiments, a 120 µl aliquot of $F_{ab}$ antibody preparation (2 mg/ml starting concentration) was added to 480 µl of the bacterial suspension and pre-incubated at room temperature for 20 min. Addition of PBS in place of the antibody preparation served as a negative control in each experiment. A 250 µl aliquot of the bacteria/antibody mixture ($2.5 \times 10^8$ bacteria/me was then added to tissue culture wells. The cells were incubated, processed, and analyzed as described above. The level of inhibition was determined by comparing the primary adherence index with and without addition of antibody. For each test bacteria/antibody preparation, a minimum of 3 experiments was performed in duplicate. In the Caco-2 adherence studies, adherence conducted in the presence of each antibody preparation was compared to that with addition of PBS, using a one-tailed Student T test, assuming unequal variance between samples. For HAI experiments, reciprocal titers between experimental groups were compared using the Wilcoxon signed rank test for paired samples (one-tailed) using XLSTAT data analysis software.

Each of four antibody preparations was assessed for ability to inhibit the adherence of strain H10407 (CFA/I) in MRHA and Caco-2 cell adherence assays. FIG. 1 (A) shows median reciprocal hemagglutination inhibition (HAI) titers of $F_{ab}$ antibodies specific for MBP, CFA/I, CfaB, $CfaE_{23-211}$ (denoted as $CfaE_N$), and $CfaE_{212-360}$ (denoted as $CfaE_C$), plotted on $\log_2$ scale. Values below a reciprocal of 2 (limit of detection) were arbitrarily plotted as 1.05 for graphing purposes. FIG. 1 (B) shows mean Caco-2 cell adherence index (% Caco-2 cells with at least 1 adherent bacterium, ±SD) of H10407 after preincubation of bacteria with $F_{ab}$ antibodies with the same specificities. All preparations were tested in at least three experiments, each done in duplicate.

The highest human A erythrocyte hemagglutination inhibition (HAI) activity was observed with $F_{ab}$ specific for $CfaE_{23-211}$, while CfaB antibodies manifest a much lower level of HAI activity (FIG. 1 (A)). No HAI activity was detectable with $F_{ab}$ antibodies against CFA/I or $CfaE_{212-360}$. Consistent findings were observed in Caco-2 cell adherence inhibition assays, in that the highest inhibitory activity was attributable to anti-$CfaE_{23-211}$ $F_{ab}$ fractions (FIG. 1(B)). In this assay anti-CFA/I $F_{ab}$ antibodies showed a lower level of inhibition, and preparations specific for CfaB and $CfaE_{212-360}$ showed no detectable effect. Taken together, these findings suggest that the most important domain for CFA/I adherence resides in the amino-terminal half of CfaE.

Figure 2:
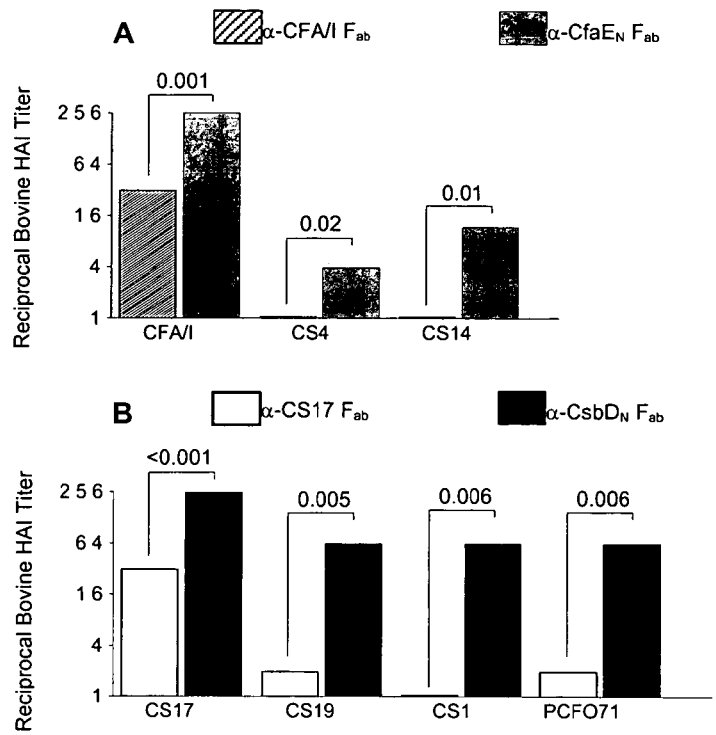
FIG. 2. Median reciprocal bovine hemagglutination inhibition (HAI) titers (plotted on $\log_2$ scale) of $F_{ab}$ antibody preparations against whole fimbriae or the amino-terminal domain of the minor fimbrial subunit of CFA/I (Panel A), and CS17 (Panel B), for ETEC type strains expressing the colonization factor indicated along the x-axis. Results represent the median of at least 4 experiments, each performed in duplicate. P values are for the differences in HAI titers between the whole fimbriae and minor subunit antibody preparations.

To test the hypothesis that evolutionary relationships would correlate with cross-reactivity of antibodies against the amino-terminal half of minor subunits representing the 5a and 5b subclasses the inhibitory effect of anti-$CfaE_{23-211}$ $F_{ab}$ on adherence of wild type strains expressing heterologous Class 5 fimbriae was assessed. Consistent with our predictions, anti-$CfaE_{23-211}$ inhibited bovine MRHA of CS4-ETEC and CS14-ETEC (FIG. 2 (A)). In comparison, anti-CFA/I $F_{ab}$ antibodies inhibited bovine MRHA of CFA/I-ETEC to a lesser degree than the anti-$CfaE_{23-211}$ while failing to inhibit MRHA of ETEC bearing CS4 or CS14. Identical results were obtained using human erythrocytes, except that anti-CFA/I $F_{ab}$ failed to display CFA/I-ETEC HAI. Neither antibody preparation inhibited bovine MRHA of ETEC bearing heterologous CFs of the other two subclasses.

These findings were corroborated by measuring the inhibitory effects of each $F_{ab}$ preparation in the Caco-2 cell adherence assay. Anti-$CfaE_{23-211}$ antibodies inhibited the adherence of CS4-ETEC and CS14-ETEC when compared to the adherence level when bacteria were pre-incubated with PBS (FIG. 3) or with anti-MBP antibodies (data not shown). The diminished adherence of CS14-ETEC did not, however, achieve statistical significance. At the same concentration, anti-CFA/I antibodies inhibited Caco-2 cell adherence of H10407 (CFA/I), though to a significantly lesser degree than did anti-$CfaE_{23-211}$ $F_{ab}$. Anti-CFA/I $F_{ab}$ did not, however, inhibit binding of ETEC bearing heterologous CFs of the same (FIG. 3) or different subclasses (data not shown).

To strengthen these findings further, we produced antibodies to the amino-terminal half of the CS17 (Subclass 5b) minor subunit CsbD and assessed its inhibitory activity along with that of anti-CS17 fimbrial antibodies in the MRHA and Caco-2 tissue culture cell model systems. Both anti-CS17 and anti-$CsbD_{19-214}$ $F_{ab}$ antibodies exhibited bovine erythrocyte HAI activity for ETEC bearing CS17, with the HAI titer of anti-$CsbD_{19-214}$ being significantly higher (FIG. 2B). Distinct from the anti-CS17 $F_{ab}$ antibodies, the anti-$CsbD_{19-214}$ $F_{ab}$ fraction also manifest significant HAI activity for ETEC bearing each of the other Subclass 5b fimbriae. Notably, the intrasubclass CF-heterologous HAI activity of anti-$CsbD_{19-214}$ antibodies was closer in magnitude to its CS17-ETEC HAI activity than for the comparable effects of anti-$CfaE_{23-211}$ antibodies. This finding was anticipated given the higher degree of identity of the minor subunits within Subclass 5b. Neither preparation inhibited bovine MRHA of ETEC bearing CFs of the other two subclasses.

Figure 3:
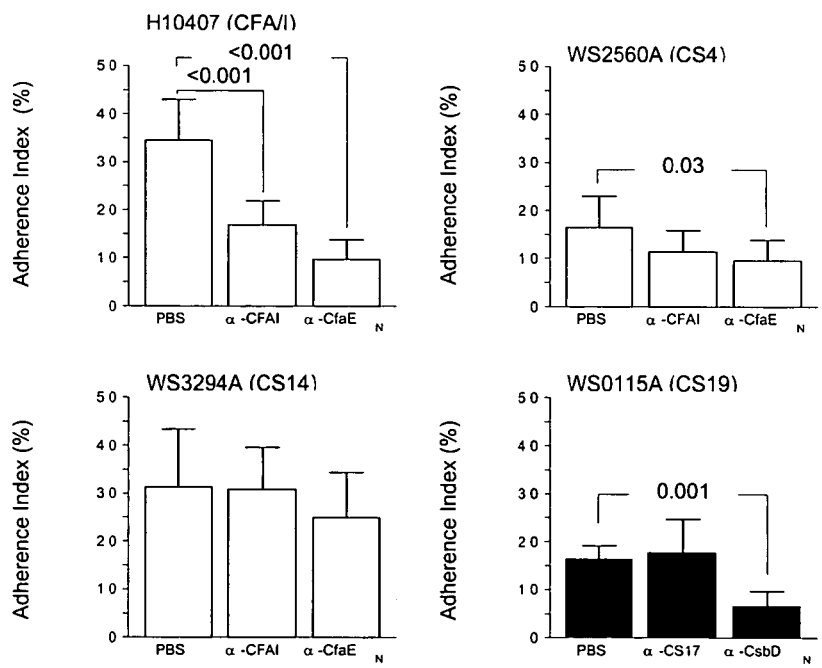
FIG. 3. Inhibitory effects of $F_{ab}$ antibodies against intact fimbriae and the N-terminal half of the minor subunit of CFA/I (open bar graphs) and CS17 (black bar graph) in Caco-2 cell adherence assays with ETEC bearing homologous (CFA/I only, upper left panel) and heterologous fimbriae.

In the Caco-2 cell adherence assay, we assessed the inhibitory effects of the same antibody preparations for CS19-ETEC, the only Subclass 5b fimbriae that appears to specifically adhere to Caco-2 cells. Here too we found that anti-$CsbD_{19-214}$ but not anti-CS17 antibodies showed significant inhibition of CS19-ETEC adherence (FIG. 3). In FIG. 3, the strain used in experiments is shown above each graph. The y-axes indicate the Caco-2 cell adherence index (percentage of Caco-2 cells with at least one adherent bacteria). Results represent the mean (±SD) of at least 3 experiments, each performed in duplicate. P values are for the differences between the negative control (PBS) and the indicated antibody preparation. Neither preparation inhibited Caco-2 cell adherence of ETEC expressing representative Subclass 5a or 5c fimbriae (data not shown).

Example 2

Conformationally Stable Donor-Strand Complemented Class 5 Adhesive Fimbrae-Adhesin Immungenic Construct Computational analyses of the CFA/I structural subunits suggests that donor strand complementation governs chaperone-subunit and subunit-subunit interaction. Therefore, we constructed a conformationally-stable construct wherein an amino-terminal donor β-strand of CfaB provides an in cis carboxy-terminal extension of CfaE to confer conformational stability and protease resistance to this molecule forming a soluble monomer capable of binding human erythrocytes.

We generated a multiple alignment of the amino acid sequences of the eight homologs of the major and minor subunits of Class 5 ETEC fimbriae to identify common structural motifs. Secondary structure prediction algorithms indicated that both subunits form an amphipathic structure rich in β-strands distributed along their length. Twenty six percent of the consensus minor subunit sequence is predicted to fold into a β-conformation, comprising 17 interspersed 13 strands, which might be expected to form a hydrophobic core.

In Cis Donor Strand Complementation of cfaE.

Two highly conserved structural motifs were identified, one of which is shared between the carboxyl termini of major and minor subunits alike and another found at the amino-terminal end of the mature (post-signal peptide cleavage) form of the major subunits. Multiple alignment of the major and minor subunits together revealed a common motif at the carboxyl terminus of each protein representing the sequence motif AGxYxGxUxUxUT(x)$_{3-6}$-COOH (SEQ ID NO: 27), where U represents any hydrophobic residue and x represents a residue of unspecified nature (FIG. 4). Sakellaris et al have previously suggested that this span denotes a β-zipper motif, analogous to that of Class I fimbrial subunits that may play a role in fimbrial subunit-chaperone interaction (37).

The major subunits of Class 5 fimbriae share a very highly conserved amino-terminal span predicted to form a β strand (FIG. 4), differing in this respect from the minor subunits. Based on its predicted structure and location, this span serves as a β-strand-like structure that is donated to neighboring CfaB subunits along the alpha-helical stalk and to CfaE at the fimbrial tip. For sequences serving as CfaB major subunit donor strand see SEQ ID No. 7. For donor strands for other adhesin monomers see SEQ ID No. 8-15.

Figure 5:
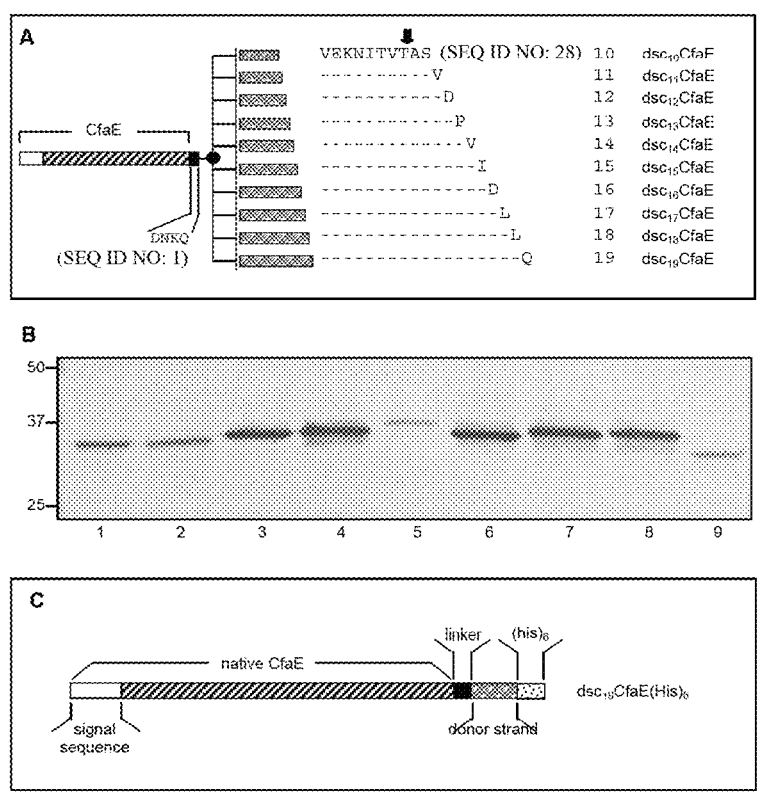
FIG. 5. Schmeatic diagrams of CfaE construct.

The highly conserved nature of the amino-terminal β strand of CfaB and its homologs, together with the precedent that the amino-terminus of type 1 fimbrial subunits functions as the exchanged donor strand in filament assembly suggested this as a good candidate for the donor β strand that noncovalently interlocks CFA/I subunits. To test this hypothesis with respect to the minor adhesive subunit, we engineered a plasmid to express a CfaE variant containing a C-terminal extension consisting of a flexible hairpin linker (DNKQ (SEQ ID No. 1) followed by the first 13 amino acid residues of mature CfaB (FIG. 5). FIG. 5 (A) illustrates, schematically, the domains of independent CfaE variant constructs with C-terminal extensions comprising the N-terminal β-strand span of CfaB varying in length from 10 to 19 residues. Each construct contains a short flexible linker peptide (DNKQ (SEQ ID NO: 1)) intercalated between the C-terminus of the native CfaE sequence and the donor β-strand. The vertical arrow identifies the donor strand valine that was modified to either a proline (V7P) to disrupt the secondary β-strand motif. FIG. 5(B) shows a western blot analysis of periplasmic concentrates from the series of strains engineered to express CfaE and the variants complemented in cis with varying lengths of the amino-terminal span of mature CfaB. The primary antibody preparations used were polyclonal rabbit antibody against CfaE. Lanes correspond to preparations from the following constructs: Lane 1, dsc10CfaE; 2, dsc11CfaE; 3, dsc12CfaE; 4, dsc13CfaE; 5, dsc13CfaE[V7P]; 6, dsc14CfaE; 7, dsc16CfaE; 8, dsc19CfaE; and 9, CfaE. Molecular weight markers (in kD) are shown to the left. FIG. 5 (C) is a schematic representation of the engineered components of dsc19CfaE(His)6, containing the native CfaE sequence (including its Sec-dependent N-terminal signal sequence), with an extension at its C-terminus consisting of a short linker sequence (i.e., DNKQ (SEQ ID NO: 1)), the 19 residue donor strand from the N-terminus of mature CfaB, and a terminal hexahistidine affinity tag.

PCR products of cfaE were inserted into plasmid vectors by in vitro recombination using the Gateway® system (Invitrogen, Carlsbad, Calif.). Primers with the following sequences were used for the initial cloning into pDONR207™: dsc-CfaE 13-1 (forward), 5'-TCG ACA ATA AAC AAG TAG AGA AAA ATA TTA CTG TAA CAG CTA GTG TTG ATC CTT AGC-3' (SEQ ID No. 16); and dsc-CfaE 13-2 (reverse), 5'-TCG AGC TAA GGA TCA ACA CTA GCT GTT ACA GTA ATA TTT TTC TCT ACT TGT TTA TTG-3' (SEQ ID No 17). The PCR products flanked by attB recombination sites were cloned into the donor vector pDONR201™ (Gateway® Technology, Invitrogen, Carlsbad, Calif.), using the Gateway BP® reaction to generate the entry vector pRA13.3. In the Gateway LR® reaction the gene sequence was further subcloned from pRA13.3 into the modified expression vector pDEST14-Kn$^r$ (vector for native expression from a T7 promoter) to generate the plasmid pRA14.2. The pDEST14-Kn$^r$ vector was constructed by modifying pDEST14® (Gateway® Technology, Invitrogen, Carlsbad, Calif.) by replacement of ampicillin with kanamycin resistance. The presence of the correct cfaE was confirmed by sequence analysis. E. coli strain BL21SI™ (Invitrogen, Carlsbad, Calif.) was used for the expression of the pRA14.1 and related CfaE donor strand complemented constructs. Cultures were grown overnight at 30° C. in LB medium without NaCl (LBON) containing 50 μg/ml kanamycin. An aliquot of the overnight culture was diluted 1:50 in LBON medium and grown at 30° C. At $OD_{600}$ of 0.5, NaCl was added to a final concentration of 200 mM, and the cells were grown at 30° C. for 3 hours. The induced cells were harvested, washed, and collected by centrifugation. Induction of protein expression was achieved by the addition of NaCl, followed by fractionation and analysis of periplasmic contents to determine the relative recovery of each protein.

We found that little CfaE was recoverable from the parent strain that expressed native CfaE, while the $dsc_{13}$CfaE construct yielded an obvious band on western blot analysis of the periplasmic fraction (FIG. 5 (B)). To confirm that the improved stability was specifically related to the 13 strand motif of the C-terminal extension, we made site-specific mutations in the central valine, changing it to either of two residues expected to break the β strand. The resultant constructs, $dsc_{13}$CfaE[V7P] and $dsc_{13}$CfaE[V7S] yielded little recoverable protein suggesting that the βstrand is important to the observed stability achieved by the 13 amino acid C-terminal extension (FIG. 5 (B)).

We then established whether a donor strand length restriction exists for stabilization of CfaE. A series of plasmids were constructed to express variants of CfaE in the same general format but with the added CfaB N-terminal β-strand varying from the first ten to as many as 19 amino acids. As shown in FIG. 5B, a donor strand length of at least the first 12 amino acids was required to achieve measurable recovery of CfaE. At the upper end of strand length, we found that as many as 19 amino acids provided the necessary information to achieve recovery of CfaE.

Chaperone-Adhesin Complex Formation and in Cis Donor Strand Complementation.

CooD, the CS1 homolog of CfaE, has been shown to form a periplasmic complex with its cognate chaperone CooB as well as with the CooA major fimbrial subunit. Analagous to type 1 fimbrial subunits, it is possible that a discrete hydrophobic groove of CooD and CfaE noncovalently interact with their respective chaperones in the process of biogenesis by the mechanism of donor strand complementation and exchange. To test such a model, we co-expressed a C-terminal hexahistidine-tagged variant of CfaA either with native CfaE or with $dsc_{19}CfaE$ and looked for the formation of bimolecular chaperone-adhesin complexes. When native CfaE was co-expressed with $CfaA(His)_6$, the two proteins co-purified upon nickel affinity chromatography, indicating the formation of a complex. In contrast, co-expression of $dsc_{19}CfaE$ with $CfaA(His)_6$ followed by affinity chromatography yielded only $CfaA(His)_6$. This suggests that the C-terminal β3 strand contributed by CfaB in cis precludes chaperone-adhesin complex formation.

Purification and Characterization of $dsc_{19}CfaE(his)_6$.

Densitometric analyses of western blots of the various dscCfaE constructs containing 13 to 19 CfaB residues revealed little difference in recovery to suggest one variant over another in terms of superior fit. To ensure that we were working with a CfaE variant with as much of its hydrophobic cleft covered as possible, we selected $dsc_{19}CfaE$ for purification and characterization. To facilitate purification, we added a hexahistidine tag to the carboxyl-terminus to yield $dsc_{19}CfaE(His)_6$, as schematically shown in FIG. 5 (C).

Figure 6:
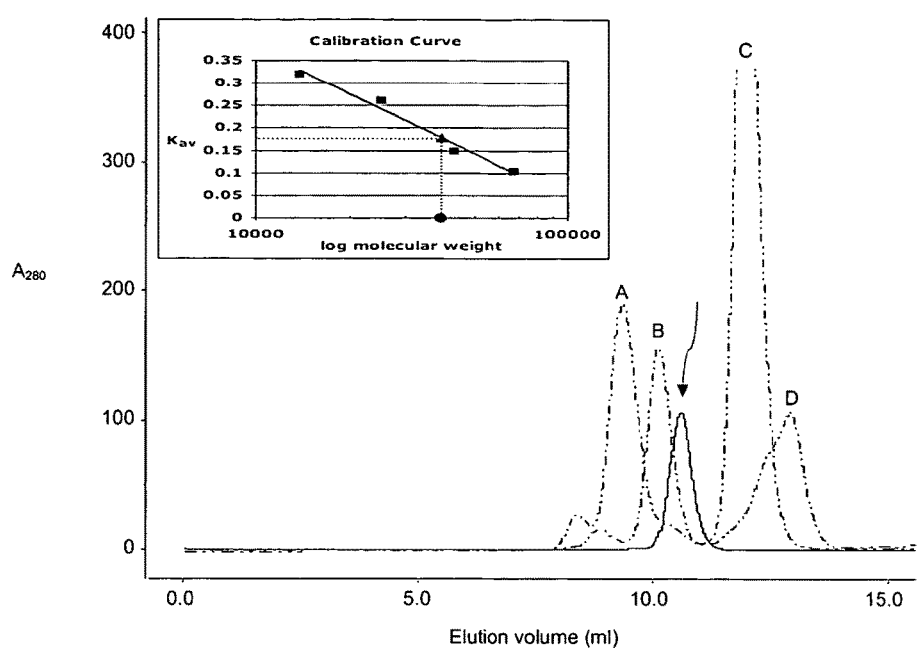
FIG. 6. Elution profile of $dsc_{19}CfaE(His)_6$ upon gel filtration with Superdex 75 (16/60) in 20 mM MES and 100 mM NaCl.

In FIG. 6, a chromatographic analysis shows elution volume of $dsc_{19}CfaE(His)_6$ (arrow), as well as molecular weight controls that include (A) albumin, 67,000 D; (B) ovalbumin, 43,000 D; (C) chymotrypsinogen A, 25,000 D; and (D) ribonuclease A, 13,700 D. Controls were separated in two different runs (B and D; and A and C), as was $dsc_{19}CfaE(His)_6$, and the three chromatograms were superimposed. The inset shows the calibration curve of derived from the 4 molecular weight standards, each of which runs as a monomer. The molecular weight of $dsc_{19}CfaE(His)_6$ was determined to be 38,961 D (see drop-down dotted line) using the formula $K_{av}=-0.1437Ln(MW)+1.6973$, where the slope and intercept were derived from the line through the standards generated by a logarithmic fit ($R^2=0.977$). This matches closely with the calculated mass of mature $dsc_{19}CfaE(His)_6$ ($M_r$, 40940).

A two-step chromatographic purification process was developed and refined using nickel affinity followed by cation exchange, which yielded soluble $dsc_{19}CfaE(His)_6$ of ca. 94% purity (FIG. 6). The results of N-terminal sequence analysis (DKNPGSENMTNTIGPHDRGG) (see SEQ ID No. 18) confirmed the identity of $dsc_{19}CfaE(His)_6$ and also validated accuracy of the signal peptide cleavage site prediction method of von Heijne (38). On gel filtration, mature $dsc_{19}CfaE(His)_6$ showed an elution profile consistent with a size of 40,869 daltons, indicating that $dsc_{19}CfaE(His)_6$ exists in a monomeric state.

Figure 7:
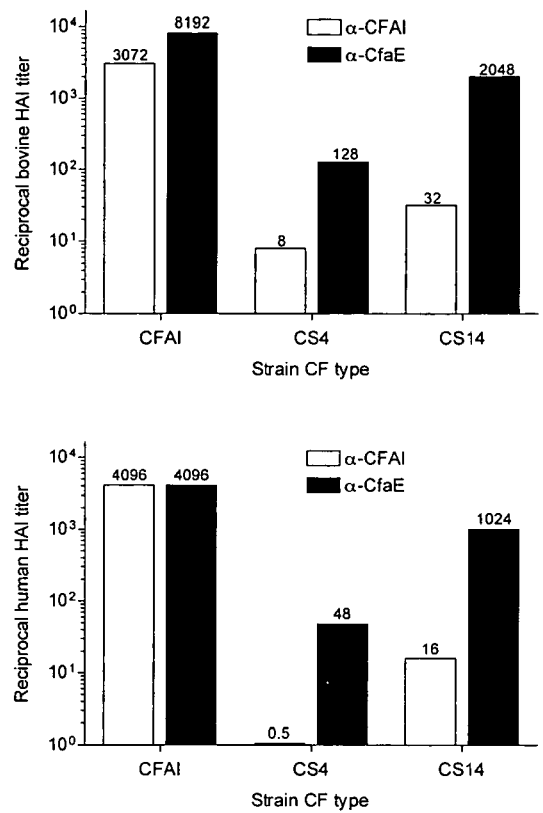
FIG. 7. Inhibitory effects of anti-CFA/I and anti-$dsc_{19}CfaE[His]6$ antiserum on mannose-resistant hemagglutination (MRHA) of CFA/I-ETEC (prototype strain H10407; LTST, CFAI, O78:H11) and ETEC that express related subclass 5a fimbriae CS4 (strain WS2560B; LTST, CS4+ CS6, O25:H−) and CS14 (strain WS3294A; ST, CS14, O78:H18).

Published evidence has indirectly implicated CfaE as the adhesive component of CFA/I fimbriae (20, 21). To directly test this premise, we adsorbed $dsc_{19}CfaE(His)_6$ onto 3 μm latex beads and tested the hemagglutination properties of these particles in the presence of mannose by MRHA (FIG. 7). In FIG. 7, the upper graph shows HAI titers of the two antisera with bovine erythrocytes and the lower panel with human type A erythrocytes. Results represent the median of at least 5 experiments, each performed in duplicate. Neither antiserum manifest HAI activity when pre-incubated with prototype ETEC that express other class 5 fimbriae of the other two subclasses. Beads coated with $dsc_{19}CfaE(His)_6$ induced MRHA of human and bovine erythrocytes. In contrast, beads coated with purified CfaB (major subunit) did not induce MRHA of human bovine or chicken erythrocytes.

Figure 8:
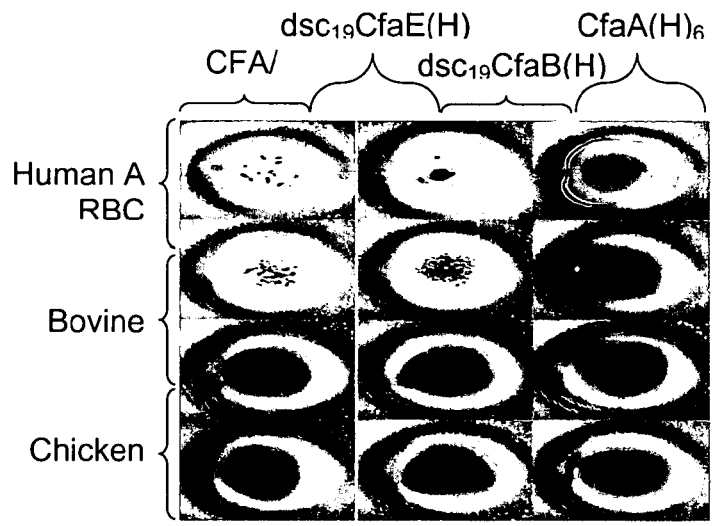
FIG. 8. Purified $dsc_{19}CfaE(His)_6$ in particulate form induces mannose-resistant hemagglutination (MRHA) of human type A and bovine erythrocytes.

To corroborate the specificity of $dsc_{19}CfaE(His)_6$ hemagglutination effect, we determined the hemagglutination inhibition (HAI) titer of rabbit polyclonal anti-$dsc_{19}CfaE$ $(His)_6$ serum against wild type CFA/I-ETEC (FIG. 8). In FIG. 8, each purified protein preparation was adsorbed to 3-um polystyrene beads, blocked with glycine, and added to 3% (vol/vol) suspension of fresh human type A (Row 1), bovine (Row 2) and chicken erythrocytes (Row 3) in porcelain tile wells. MRHA was visually determined after 20 minutes of rockling on ice. Column 2 shows human and bovine MRHA positive phenotype of $dsc_{19}CfaE(His)_6$ and Column 3 shows the corresponding negative MRHA phenotypes of the CFA/I major subunit $dsc_{19}CfaB(His)_6$. CFA/I native fimbriae (Column 1) and the CFA/I periplasmic chaperone protein $CfaA(His)_6$ (Column 4) served as positive and negative controls, respectively.

As shown in FIG. 8, the anti-$dsc_{19}CfaE(His)_6$ serum exhibited a median HAI titer of 1:12,288, six-fold greater but not statistically different than the median HAI titer of anti-CFA/I serum. Anti-$dsc_{19}CfaE(His)_6$ serum also registered HAI titers exceeding those of CFA/I antiserum against bacteria that expressed CS4 and CS14, the two Class 5 fimbriae of the same subclass as CFA/I (FIG. 8). Neither of these antisera revealed detectable HAI titers against bacteria that express fimbriae of the two other defined Class 5 subgroups.

Ultrastructural Localization of CfaE in CFA/I Fimbriae.

It was previously suggested that CfaE localizes to the distal tip of CFA/I fimbriae based on inference from genetic manipulations and crude bacterial surface fractionation studies (34). However, the imprecision of these approaches has left the question of CfaE localization open to debate. Using high-titer polyclonal antiserum raised against CfaE as the primary antibody in immunoelectron microscopy (IEM), a pattern of decoration was found that definitively supports localization at the outermost tips of peritrichous CFA/I fimbriae.

Example 3

Method for the Induction of Immunity to Conformationally Stable Class 5 Adhesin Construct The adhesins, located on the distal tip of fimbriae of certain *E. coli* are the most important component for the induction of diarrheagenic *E. coli* bacterial immunity. However, fimbrial adhesins are inherently unstable and subject to degradation when devoid of their non-covalent linkage to major subunits fimbrial components. Therefore, improvements in conferring of protease resistance and conformational stability is important for production of maximally effective induction of B-cell activity capable of conferring anti-adhesive immunity against *E. coli*, including enterotoxigenic *E. coli*.

An aspect of this invention is the construction of stable polypeptide construct, as shown in Example 2. As taught in Example 1, protection against pathology caused by *E. coli* can be mediated by inhibition of colonization of bacteria by sterically hindering adhesion of fimbriae, and therefore bacteria, by induction of a specific B-cell response to adhesin polypeptide regions. Another aspect of this invention, therefore, is the induction of immunity by administration of a conformationally-stable polypeptide construct.

The construct comprises an antigenic fragment comprising an adhesin polypeptide sequence linked at the C-terminal regions to a linker that is itself operatively linked, at its C-terminal end, to a polypeptide of a major structural fimbrial subunit, such as CfaB. The antigenic fragment can be comprised of adhesin polypeptide sequences encoding any *E. coli* adhesin or adhesin fragment or alternatively polymers of adhesin polypeptides. Adhesins are selected from the group consisting of CfaE, CsfD, CsuD, CooD, CosD, CsdD, CsbD and CotD.

The method for induction of anti-adhesin-mediated colonization of diarrheagenic bacteria contains the following steps:
  a. priming is by administration of immunogen containing said conformationally-stable adhesin polypeptide construct. Immunogen can be administered orally, nasally, subcutaneously, intradermally, transdermally, transcutaneously intramuscularly, or rectally. The range of a unit dose of immunogen is 50 µg to 1 mg of immunogen. The immunogen is administered in any number of solutions with or without carrier protein or adjuvant or adsorbed into particles such as microspheres;
  b. Subsequent to a priming dose, 2 to 4 boosting doses are also administered with unit dose range of 50 µg to 1 mg of immunogen in a buffered aqueous solution.

An alternative vaccine approach is the administration of the DNA construct described in Example 2 but inserted and expressed in host bacterial cells. The recombinant host cells can then be administered as a whole cell vaccine in order to confer immunity not only to the host cell but against the expressed ETEC recombinant adhesin polypeptides. Representative host cells include, but are not limited to *Escherichia coli*, members of the genus *Shigella*, members of the genus *Campylobacter*, members of the genus *Salmonella*, members of the genus *Vibrio* including *Vibrio cholerae*.

A method for the induction of whole cell immunity contains the following steps:
  a. administration of a priming dose comprising an adequate numbers of whole cell bacteria, selected from the group consisting of *Escherchia coli*, *Shigella* spp, *Camplylobacter* spp, *Vibrio* spp and *Vibrio cholerae*, such that the expressed recombinant adhesin polypeptide is 50 µg to 1 mg per dose.
  b. Subsequent to priming dose, administration of 1 to 4 boosting doses of whole cell bacteria, selected from the group consisting of *Escherchia coli*, *Shigella* spp, *Camplylobacter* spp, *Vibrio* spp and *Vibrio cholerae*, such that the expressed recombinant adhesin polypeptide is in the range of 50 µg to 1 mg per dose. Alternatively, the boosting doses can be immunogen containing said protease resistant adhesin peptide construct a unit dose range of 50 µg to 1 mg of immunogen in a buffered aqueous solution.

Figure 9:
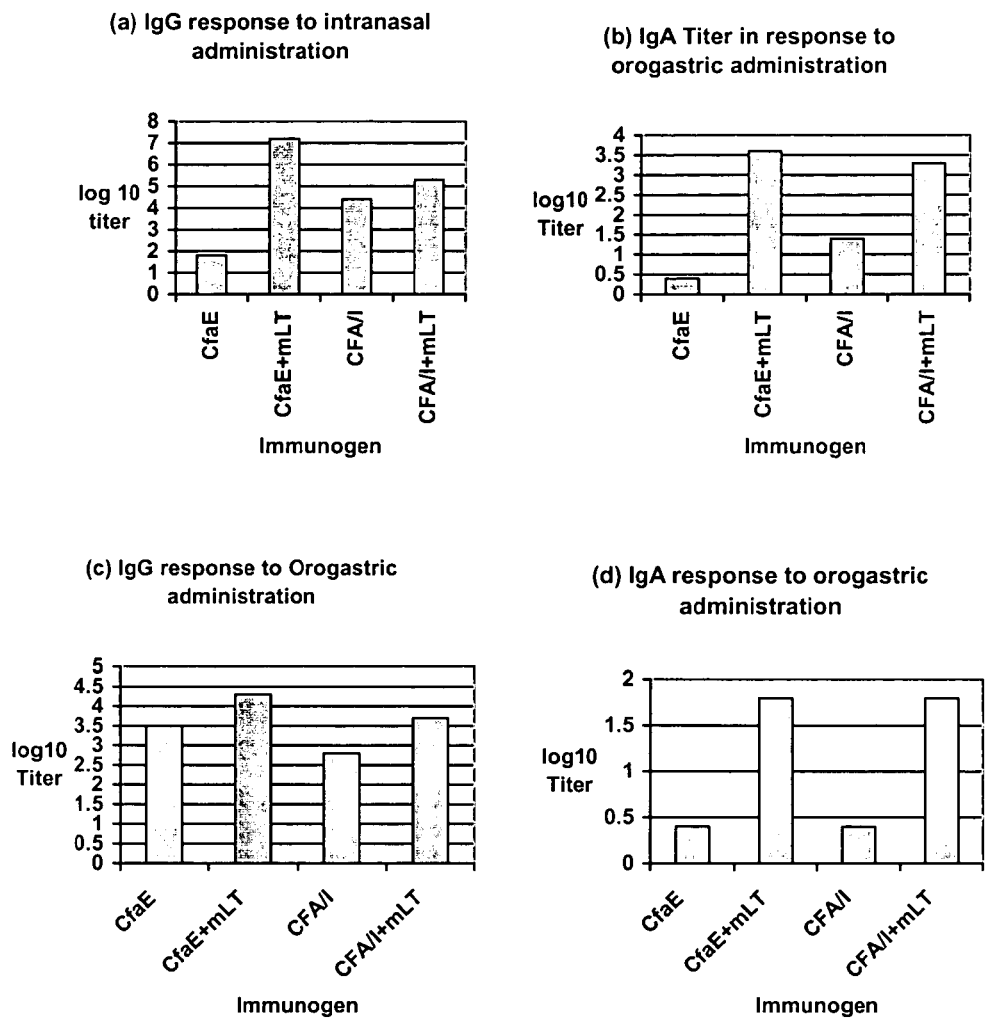
FIG. 9. Antibody induction following orogastric or intranasal administration in mice of dscCfaE plus mLT or CFA/I plus mLT.

As a specific example in order to illustrate the method, the construct described in Example 2 was utilized to induce an immune response in mice. FIG. 9 shows IgG and IgA responses to homologous antigen in ELISA following either orogastric or intranasal administration of CfaE, CfaE plus mLT, CFA/I or CFA/I plus mLT. In FIG. 9, groups of mice (n=6) were administered three (3) doses at 2 week intervals of either fimbria (CFA/I) (250 µg), CFA/I (250 µg) plus mLT (mLT=*E. coli* heat labile toxin LTR192G) (10 µg), dscCfaE (250 µg) or dscCfaE (250 µg) plus mLT mLT=LTR192G (10 µg). Serum was collected approximately 42 hours after the initial immunization. As illustrated in FIG. 9, CfaE or fimbria (CFA/I) induced a vigorous IgG and IgA response and significantly enhanced by the simultaneous administration of mLT. Interestingly, the simultaneous administration of mLT with CfaE or fimbria (CFA/I), intranasally or orogastrically, yielded a greater overall antibody response for CfaE than for CFA/I.

Figure 10:
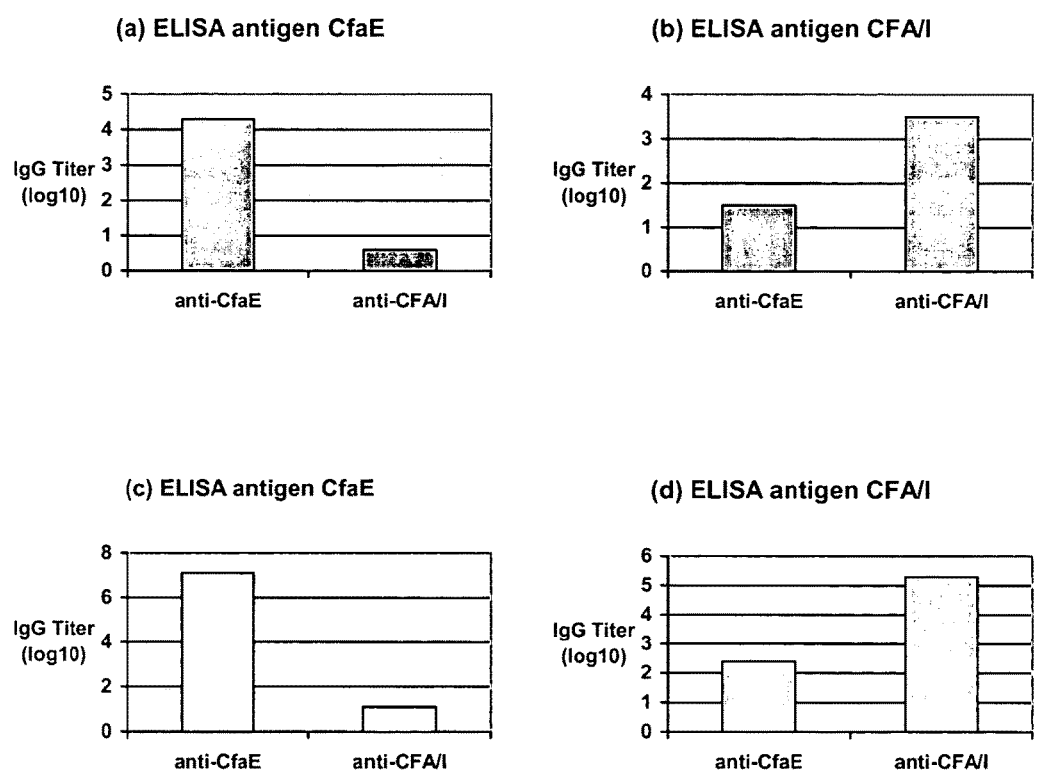
FIG. 10. Anti-CfaE and anti-CFA/I ELISA binding activity by ELISA using either dscCfaE or CFA/I as antigen.

FIG. 10 illustrates antibody titers specific to either CfaE or CFA/I induced following administration of CfaE verses CFA/I, either with mLT. As in FIG. 9, groups of mice (n=6) were administered three (3) doses at 2 week intervals of either CFA/I (250 µg) plus mLT (mLT=*E. coli* heat labile toxin LTR192G) (10 µg) or dscCfaE (250 µg) plus mLT mLT=LTR 192G (10 µg). Following immunization, serum antibody titers were measured by ELISA using homologous antigen. FIGS. 10 (*a*) and (*b*) show antibody titers induced following orogastric administration of either CfaE plus mLT and FIGS. 10 (*c*) and (*d*) show antibody titers induced following intranasal administration. Following either orogastric or intranasal administration of CfaE and CFA/I plus mLT, immunization with dscCfaE resulted in a higher titer of specific IgG antibody response. These data indicate that dscCfaE is an effective, when administered at least via the intranasal and orogastric route, at inducing an immune response.

Figure 11:
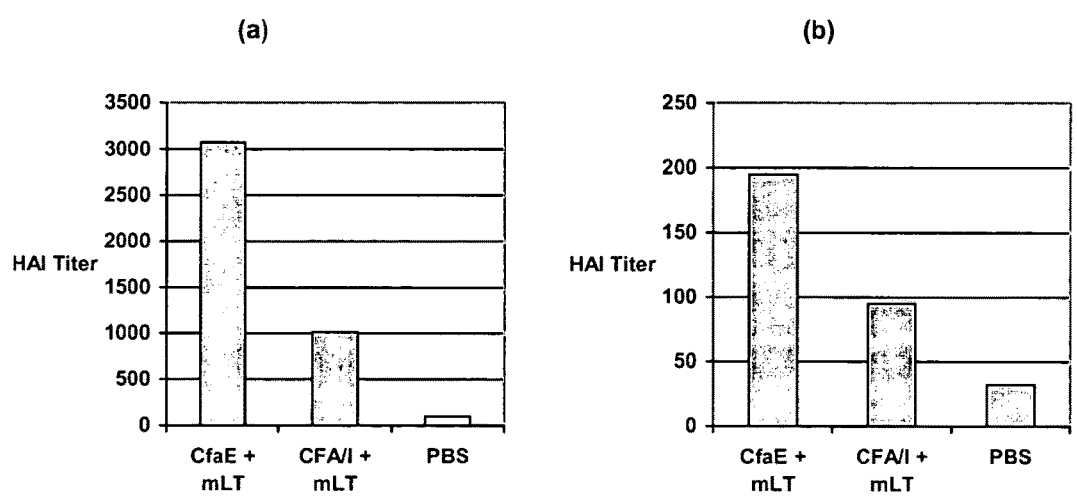
FIG. 11. HAI activity of serum from mice immunized with dscCfaE plus mLT or CFA/I plus mLT.

As illustrated in FIG. 10, dscCfaE can effectively induce a high titer of antibody. To ascertain if the antibody was functional, analysis of the serum antibody is illustrated in FIG. 11. FIG. 11 (*a*) shows the HAI titer of serum obtained following intranasal administration of either CFA/I or CfaE and FIG. 11 (*b*) shows the HAI response of serum obtained following orogastric administration. As illustrated by FIG. 11, immunization with CfaE induced much more robust inhibitory activity than CFA/I, regardless of the route of administration. The increased functional activity is correlated with the titer of anti-CfaE antibody represented in the serum. Collectively, these data illustrate that the dscCfaE construct is capable of inducing high titers of functional antibody.

Example 4

Method for the Induction of Immunity to Class 5 Fimbriae Adhesin

An aspect of this invention is that the most important component of *E. coli* fimbriae for inducing an immune response against *E. coli* capable of effectively preventing bacterial pathology is adhesin (as taught in Example 1). These molecules are located on the distal tip of native fimbriae. It is important, therefore, to induce immunity, principally a B-cell response with concomitant production of immunoglobulin specific for adhesin molecule regions capable of inhibiting adhesin attachment to host cells (see inhibition of adhesin in example 1).

Immunoglobulin-mediated immunity can be effected by steric hindrance caused by binding at or near the active host-cell binding site or by binding to epitopes remote from adhesin host-cell binding site. A method for the induction of anti-adhesin mediated colonization of diarrheagenic bacteria contains the following steps:
  a. priming is by administration of immunogen comprising whole fimbriae containing adhesin. Alternatively, isolated fragments of fimbriae, containing adhesin or adhesin polypeptides alone, can be used rather than intact fimbriae. Immunogen can be administered orally, nasally, subcutaneously, intradermally, transdermally, transcutaneously intramuscularly, or rectally. The range of a unit dose of immunogen is 50 µg to 1 mg of immunogen. The immunogen is administered in any number of aqueous buffered solutions with or without carrier protein or adjuvant;

b. Subsequent to a priming dose, 2 to 4 boosting doses are also administered with unit dose range of 50 µg to 1 mg of immunogen in a buffered aqueous solutions.

Referring to FIG. 9, either orogastric or intranasal administration of CFA/I, with or without the adjuvant mLT induced a significant serum IgG response following a three (3) dose regimen. As previously described, groups of mice (n=6) were administered three (3) doses at 2 week intervals of either CFA/I (250 µg), CFA/I (250 µg) plus mLT (mLT=LTR192G) (10 µg), dscCfaE (250 µg) or dscCfaE (250 µg) plus mLT mLT=LTR 192G (10 µg). Notwithstanding the robust antibody response following immunization with fimbria (i.e. CFA/I), as illustrated in FIG. 9 and FIG. 10, anti-CFA/I serum contained a modest anti-CfaE activity as illustrated in FIG. 10. Consistent with this observation, referring to FIG. 11, a significant HM titer was also seen using the serum antibody obtain following CFA/I administration. Nevertheless, the antibody and HAI responses to CFA/I, which contains an adhesin tip, is much less than that obtained when stable CfaE (dscCfaE) is used as immunogen, as illustrated in FIG. 10 and FIG. 11.

Example 5

Induction of Anti-ETEC Immunity Using an Anti-CS3 Construct

CS3 is composed of two distinct subunits, CstH and CstG (Savarino, unpublished). This conclusion is contrary to earlier published observations and conclusions (39, 40). Purified CS3 from wild type ETEC strain M424C1 (LTST-CS1+CS3-06:H16) was resolved into two closely migrating protein bands on SDS-PAGE, each with distinct N-terminal amino acid sequences. DNA sequence analysis of the M424C1 CS3 gene cluster revealed two contiguous open reading frames (ORFs) at the 3-prime end of the cluster that encode the proteins CstH and CstG whose N-terminal regions match exactly with the two experimentally derived N-terminal sequences of CS3 (Savarino S J, unpublished data). These two subunits share 46% similarity and appear to be present in purified fimbriae in a ratio of nearly 1:1.5, as compared to the estimated ratio of 1:1000 for the CfaE/CfaB minor and major subunits, respectively, of CFA/I (37).

Figure 12:
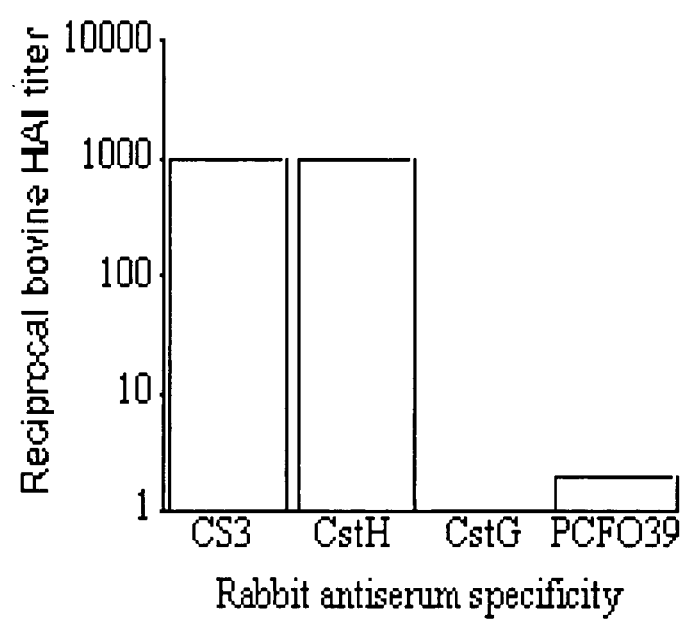
FIG. 12. Hemagglutination inhibition of rabbit polyclonal antiserum generated against native CS3, purified CstH, CstG and PCFO39 fimbriae.

By mutation and complementation experiments, we found that both CstH and CstG subunits are necessary for expression of CS3 fibrillae. Recombinant plasmids were engineered to express MBP fusions to the signal peptide-cleaved forms of CstH and CstG, and each was used to generate rabbit polyclonal antibodies. Preincubation of purified IgG and Fab fractions from the anti-MBPCstH but not anti-MBPCstG with wild type CS3-ETEC (strain WS2010A) inhibited bovine erythrocyte MRHA, the surrogate in vitro binding phenotype of CS3. We also engineered fusions of CstH and CstG to an intein carrier (41), and purified these passenger proteins by chitin affinity chromatography (New England Biolabs, Ipwich, Mass.) and in-column autocleavage at the intein-passenger protein junction. Rabbit polyclonal antisera generated against purified CstH but not CstG also exhibited hemagglutination inhibition (HAI) activity, corroborating the results observed with antibodies against the corresponding MBP fusions (see FIG. 12). In FIG. 12, reactivity to PCFO39 fimbriae was included as a negative control. Our results support the contention that CstH is the actual binding subunit of CS3 and hence may serve as a precise vaccine target for generating anti-adhesive humoral immune responses.

Based on the available evidence indicating that CstH is the CS3 adhesin, we undertook efforts to engineer a stable CstH construct. As mentioned, we cloned CstH as a C-terminal fusion to intein (IMPACT-CN™ expression system, New England Biolabs™). This system offered reasonable yields and purity of CstH at the 1 L flask culture level. Scale-up to a 10 L fermentor resulted in high-level expression of the intein-CstH fusion product, however, was largely confined to the insoluble fraction after cell disruption, making this less suitable as a system for intermediate or large-scale production efforts. The untagged, mature form of CstH that we derived from use of this system did, however permitted protein characterization.

Native gel electrophoresis and size exclusion chromatography indicated that CstH self-assembles into oligomers by ordered, noncovalent interaction with a (with a mass range indicating formation of CstH 4-16mers). High resolution electron microscopy to demonstrated two distinct morphologic forms. CstH oligomers were observed as either globular or linear particles, and each type showed some variation in size and arrangement.

While CstH particle formation may confer some favorable immunologic properties, the apparent heterogeneity of such a preparation poses potential difficulties as it relates to developing a reproducible manufacturing process with defined end-product characteristics. Therefore, donor strand complementation was utilized in order to design stable CstH constructs.

The CS3 fibrillar assembly has been classified as a member of the classical chaperone-usher (CU) pathway based on the genetic relatedness of the CS3 periplasmic chaperone to the PapD superfamily (42). Interestingly, it falls into the FGL (F1-G1 long) subfamily, referring to a characteristic structural feature of the chaperone, which mediates assembly of thin fibrillar or afimbrial adhesive organelles (43). Alignment of the N-terminal amino acid span of CstH with *Yersinia pestis* F1 capsule subunit reveals a common motif of alternating hydrophobic residues through amino acid 16 (with reference to the mature CstH polypeptide). This span of the F1 capsular subunit (Caf1) functions as the donor strand, interacting with the Caf1M chaperone and neighboring F1 protein subunits during capsular assembly and subunit articulation (44).

Figure 13:
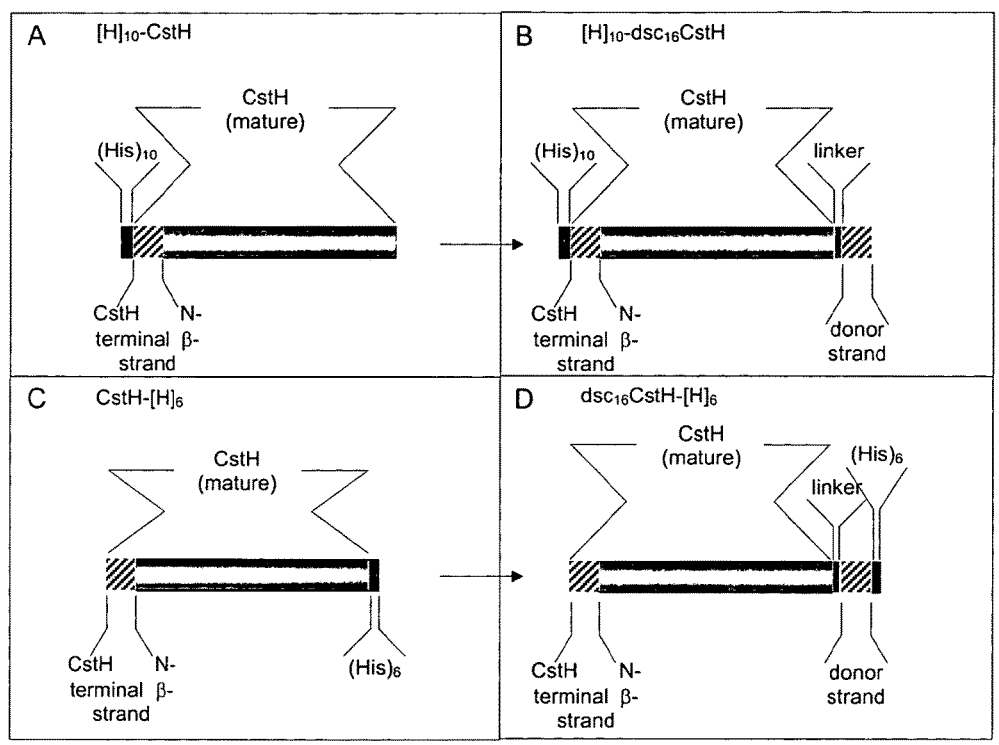
FIG. 13. Schematic representation of components of CstH construct. Panel A, illustrates mature CstH of CS3 with histidine tag attached at its N-terminal end. Panel B illustrates the construct in panel A but with a short linker polypeptide attached at the C-terminal end of the mature CstH construct which in-turn has a duplicated 16 amino acid CstH N-terminal region attached at its C-terminus. Panel C illustrates the construct of Panel A but with a (His)$_6$ tag inserted at the C-terminus, verses at the N-terminus. Panel D illustrates a similar construct as in Panel B but with a smaller (His)$_6$ on the C-terminus of the duplicated CstH region donor strand verses a (His)$_{10}$ at the N-terminus.

Reasoning that the corresponding CstH segment may function in a similar fashion, two in-cis donor strand complemented CstH constructs were engineered. The full-length CstH sequence (SEQ ID No. 19) contains a 22 amino acid signal peptide that is normally cleaved upon entry into the periplasm to give the mature CstH sequence (SEQ ID No. 23). The mature sequence also contains a 16 amino acid terminal β-strand disclosed in SEQ ID No. 20. FIG. 13 schematically illustrates the construct design. FIG. 13 (A) and FIG. 13 (C) illustrate the mature CstH amino acid sequence, but with the 22 amino acid leader sequence removed and a His-tag inserted. In FIG. 13 (A), a $[His]_{10}$ tag is inserted to the N terminus of the mature CstH. In FIG. 13 (C), a $[His]_6$ tag is inserted to the C-terminal end of the mature CstH.

FIGS. 13 (B) and (D) illustrate further modifications. FIG. 13 (B) illustrates the construct $[His]_{10}dsc_{10}CstH$, disclosed in SEQ ID No. 21. $[His]_{10}dsc_{10}CstH$ contains an N-terminal $His_{10}$, as in FIG. 13 (A) but with a short hairpin linker (SEQ ID No 1, 2 or 3) fused to the C-terminal end of the mature CstH which is in-turn fused at its C-terminal end to a duplicated donor strand derived from the first 16 amino acids from the CstH terminus disclosed in SEQ ID No. 20. FIG. 13 (D) schematically illustrates $dsc_{16}CstH[His]_6$, which is disclosed as SEQ ID No. 22. This construct contains a His-tag at the C-terminus, verses at the N-terminal end, as in $[His]_{10}dsc_{16}CstH$. The two amino acids between the C-terminal end of the in cis donor strand and the His-tag are derived from the expression vector multicloning side coding sequence. The $[His]_{10}dsc_{10}CstH$ construct was inserted into the T7 expression plasmid pET 19 and is referred to pET19/$[His]_{10}dsc_{16}CstH$. Similarly, the $dsc_{16}CstH[His]_6$ construct was inserted into pET24 and is referred to as pET24/$dsc_{16}$-CstH$[His]_6$. The $dsc_{16}CstH[His]_6$ construct exhibited high solubility.

Figure 14:
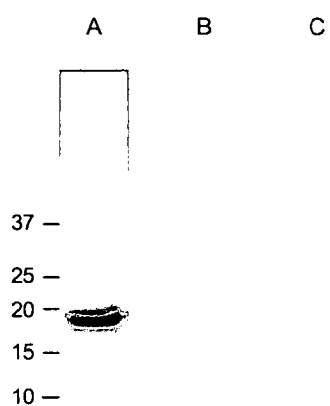
FIG. 14. SDS PAGE and western blot analysis of purified dsc$_{16}$CstH[His]$_6$.

Electrophoretic analysis demonstrated that the expressed construct exhibited monomeric characteristics as illustrated in FIG. 14. In FIG. 14 (A), SDS-polyacrylamide gel electrophoresis (SDS-PAGE) shows a clear prominent band. Western blot analysis using anti-CstH and anti-CS3 (FIGS. 14 (B) and (C)), respectively, also show a clearly prominent monomeric band.

The CS3 construct is contemplated to be utilized by a method similar to that described in Example 3. Therefore, induction of immunity using $dsc_{16}CstH$-[His]6, or other variants, is by the method comprising the steps:
 a. priming is by administration of the $[His]_{10}dsc_{16}CstH$ or $dsc_{16}CstH$-[His]6 (i.e. SEQ ID No. 21 or SEQ ID No. 22) immunogen or variants (as illustrated in FIG. 13) containing said conformationally-stable adhesin polypeptide construct. Immunogen can be administered orally, nasally, subcutaneously, intradermally, transdermally, transcutaneously intramuscularly, or rectally. The range of a unit dose of immunogen is 50 µg to 1 mg of immunogen. The immunogen is administered in any number of solutions with or without carrier protein or adjuvant or adsorbed into particles such as microspheres;
 b. Subsequent to a priming dose, 2 to 4 boosting doses are also administered with unit dose range of 50 µg to 1 mg of immunogen in a buffered aqueous solution.

The CstH construct can also be used expressed in host bacterial cells including *Escherichia coli*, members of the genus *Shigella*, members of the genus *Campylobacter*, members of the genus *Salmonella*, members of the genus *Vibrio* including *Vibrio cholerae* as described for the class 5 adhesin construct in Example 3.

REFERENCES

1. Black, R. E. 1990. Epidemiology of travelers' diarrhea and relative importance of various pathogens. Rev Infect Dis 12 (Suppl 1):S73-S79.
2. Huilan, S., L. G. Zhen, M. M. Mathan, M. M. Mathew, J. Olarte, R. Espejo, U. Khin Maung, M. A. Ghafoor, M. A. Khan, Z. Sami, and et al. 1991. Etiology of acute diarrhoea among children in developing countries: a multicentre study in five countries. Bull World Health Organ 69:549-55.
3. Nataro, J. P., and J. B. Kaper. 1998. Diarrheagenic *Escherichia coli*. Clin Microbiol Rev 11:142-201.
4. Gaastra, W., and A. M. Svennerholm. 1996. Colonization factors of human enterotoxigenic *Escherichia coli* (ETEC). Trends Microbiol 4:444-452.
5. Evans, D. G., R. P. Silver, D. J. Evans, Jr., D. G. Chase, and S. L. Gorbach. 1975. Plasmid-controlled colonization factor associated with virulence in *Esherichia coli* enterotoxigenic for humans. Infect Immun 12:656-667.
6. Grewal, H. M., H. Valvatne, M. K. Bhan, L. van Dijk, W. Gaastra, and H. Sommerfelt. 1997. A new putative fimbrial colonization factor, CS19, of human enterotoxigenic *Escherichia coli*. Infect Immun 65:507-513.
7. Khalil, S. B., F. J. Cassels, H. I. Shaheen, L. K. Pannell, K. A. Kamal, B. T. Pittner, M. Mansour, R. Frenck, S. J. Savarino, and P. L. F. 2000. Presented at the 100th General Meeting of the American Society for Microbiology, Los Angeles, Calif.
8. Froehlich, B. J., A. Karakashian, L. R. Melsen, J. C. Wakefield, and J. R. Scott. 1994. CooC and CooD are required for assembly of CS1 pili. Mol Microbiol 12:387-401.
9. Froehlich, B. J., A. Karakashian, H. Sakellaris, and J. R. Scott. 1995. Genes for CS2 pili of enterotoxigenic *Escherichia coli* and their interchangeability with those for CS1 pili. Infect Immun 63:4849-56.
10. Jordi, B. J. A. M., G. A. Willshaw, A. M. van der Zeijst, and W. Gaastra. 1992. The complete nucleotide sequence of region 1 of the CFA/I fimbrial operon of human enterotoxigenic *Escherichia coli*. DNA Seq 2:257-263.
11. Perez-Casal, J., J. S. Swartley, and J. R. Scott. 1990. Gene encoding the major subunit of CS1 pili of human enterotoxigenic *Escherichia coli*. Infect Immun 58:3594-3600.
12. Scott, J. R., J. C. Wakefield, P. W. Russell, P. E. Orndorff, and B. J. Froehlich. 1992. CooB is required for assembly but not transport of CS1 pilin. Mol Microbiol 6:293-300.
13. Gaastra, W., H. Sommerfelt, L. van Dijk, J. G. Kusters, A. M. Svennerholm, and H. M. Grewal. 2002. Antigenic variation within the subunit protein of members of the colonization factor antigen I group of fimbrial proteins in human enterotoxigenic *Escherichia coli*. Int J Med Microbiol 292:43-50.
14. Ramer, S. W., G. K. Schoolnik, C. Y. Wu, J. Hwang, S. A. Schmidt, and D. Bieber. 2002. The Type IV pilus assembly complex: Biogenic interactions among the bundle forming pilus proteins of enteropathogenic *Escherichia coli*. J Bacteriol 184:3457-65.
15. Soto, G. E., and S. J. Hultgren. 1999. Bacterial adhesins: common themes and variations in architecture and assembly. J Bacteriol 181:1059-1071.
16. Low, D., B. Braaten, and M. Van der Woude. 1996. Fimbriae, p. 146-157. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (ed.), *Escherichia coli* and *Salmonella*: Cellular and Molecular Biology, 2nd ed, vol. Volume 1. ASM Press, Washington, D.C.
17. Sakellaris, H., and J. R. Scott. 1998. New tools in an old trade: CS1 pilus morphogenesis. Mol Microbiol 30:681-7.
18. Sakellaris, H., V. R. Penumalli, and J. R. Scott. 1999. The level of expression of the minor pilin subunit, CooD, determines the number of CS1 pili assembled on the cell surface of *Escherichia coli*. J Bacteriol 181:1694-7.
19. Buhler, T., H. Hoschutzky, and K. Jann. 1991. Analysis of colonization factor antigen I, an adhesin of enterotoxigenic *Escherichia coli* 078:H11: fimbrial morphology and location of the receptor-binding site. Infect Immun 59:3876-3882.
20. Sakellaris, H., G. P. Munson, and J. R. Scott. 1999. A conserved residue in the tip proteins of CS1 and CFA/I pili of enterotoxigenic *Escherichia coli* that is essential for adherence. Proc Natl Acad Sci, USA 96:12828-12832.

21. Anantha, Ravi P., A. L. McVeigh, L. H. Lee, M. K. Agnew, F. J. Cassels, D. A. Scott, T S. Whittam, and S. J. Savarino. 2004. Evolutionary and functional relationships of colonization factor antigen I and other class 5 adhesive fimbriae of enterotoxigenic *Escherichia coli*. Inf and Imm. 72: 7190-7201.

22. Viboud, G. I., M. M. McConnell, A. Helander, and A. M. Svennerholm. 1996. Binding of enterotoxigenic *Escherichia coli* expressing different colonization factors to tissue-cultured Caco-2 cells and to isolated human enterocytes. Microb Pathogen 21:139 147.

23. Kuehn M J, J. Heuser, S. Normark and S. J. Hultgren. 1992. P pili in uropathogenic *E. coli* are composite fibres with distinct fibrillar adhesive tips. Nature 356:252-5.

24. Sauer F G, K. Futterer, J. S. Pinkner, K. W. Dodson, S. J. Hultgren and G. Waksman. 1999. Structural basis of chaperone function and pilus biogenesis. Science 285: 1058-61.

25. Choudhury D, A. Thompson, V. Stojanoff, et al. X-ray structure of the FimC-FimH chaperone-adhesin complex from uropathogenic *Escherichia coli*. Science 1999; 285: 1061-6.

26. Barnhart M M, Pinkner J S, Soto G E, et al. From the cover: PapD-like chaperones provide the missing information for folding of pilin proteins. Proc. Natl. Acad. Sci. U.S.A. 2000; 97:7709-14.

27. Krasan G P, Sauer F G, Cutter D, et al. Evidence for donor strand complementation in the biogenesis of *Haemophilus influenzae* haemagglutinating pili. Mol. Microbiol. 2000; 35:1335-47.

28. Zavialov A V, Kersley J, Korpela T, Zav'yalov VP, MacIntyre S and Knight S D. Donor strand complementation mechanism in the biogenesis of non-pilus systems. Mol. Microbiol. 2002; 45:983-995.

29. Rao, M. R., R. Abu-Elyazeed, S. J. Savarino, A. B. Naficy, T. F. Wierzba, I. Abdel Messih, H. Shaheen, R. W. Frenck, A. M. Svennerholm, and J. D. Clemens. 2003. High disease burden due to enterotoxigenic *Escherichia coli* diarrhea in early life among rural Egyptian children. J Clin Microbiol 41:4862-4864.

30. Cravioto, A., S. M. Scotland, and B. Rowe. 1982. Hemagglutination activity and colonization factor antigens I and II in enterotoxigenic and non enterotoxigenic *Escherichia coli* isolated from humans. Infect Immun 36:189-197.

31. Sambrook, J., E. F. Fritsch, and T. Maniatis. 1989. Molecular Cloning: A Laboratory Manual, 2nd ed. Cold Spring Harbor Laboratory Press, Cold Spring Harbor, N.Y.

32. Evans, D. G., D. J. Evans, Jr., W. S. Tjoa, and H. L. DuPont. 1978. Detection and characterization of colonization factor of enterotoxigenic *Escherichia coli* isolated from adults with diarrhea. Infect Immun 19:727-736.

33. Darfeuille-Michaud, A., D. Aubel, G. Chauviere, C. Rich, M. Bourges, A. Servin, and B. Joly. 1990. Adhesion of enterotoxigenic *Escherichia coli* to the human colon carcinoma cell line Caco-2 in culture. Infect Immun 58:893-902.

34. Khalil, S. B., F. J. Cassels, H. I. Shaheen, L. K. Pannell, N. El-Ghorab, K. Kamal, M. Mansour, S. J. Savarino, and L. F. Peruski, Jr. 1999. Characterization of an enterotoxigenic *Escherichia coli* strain from Africa expressing a putative colonization factor. Infect Immun 67:4019-4026.

35. Hall, R. H., D. R. Maneval, Jr., J. H. Collins, J. L. Theibert, and M. M. Levine. 1989. Purification and analysis of colonization factor antigen I, *coli* surface antigen 1, and *coli* surface antigen 3 fimbriae from enterotoxigenic *Escherichia coli*. J Bacteriol 171:6372 6374.

36. Hess, S., F. J. Cassels, and L. K. Pannell. 2002. Identification and characterization of hydrophobic *Escherichia coli* virulence proteins by liquid chromatography-electrospray ionization mass spectrometry. Anal Biochem 302: 123-130.

37. Sakellaris H, D. P. Balding and J. R. Scott. 1996. Assembly proteins of CS1 pili of enterotoxigenic *Escherichia coli*. Mol. Microbiol. 21:529-41.

38. Bendtsen J. D., H. Nielsen H, G. von Heijne and S. Brunak. 2004. Improved prediction of signal peptides: SignalP 3.0. J Mol Biol 340:783-95.

39. Hall, R. H., D. R. Maneval, Jr., J. H. Collins, J. L. Theibert, J. L. and M. M. Levine. 1989. Purification and analysis of colonization factor antigen I, *coli* surface antigen 1, and *coli* surface antigen 3 fimbriae from enterotoxigenic *Escherichia coli*. J. Bact. 171:6372-6374.

40. Jalajakumari, M. B., C. J. Thomas, R. Halter, and P. A. Manning. 1989. Genes for biosysnthesis and assembly of CS3 pili of CFA/II enterotoigenic *Escherichia coli*: novel regulation of pilus production by bypassing an amber codon. Mol. Micro 3:1685-1695.

41. Perler, F. B. 2002. InBase, the Intein Database. Nuc. Acids. Res. 30:383-384.

42. Hung, D. L., S. D. Knight, R. M. Woods, J. S. Pinkner and S. J. Hultgren. 1996. Molecular basis of two subfamilies of immunoglobulin-like chaperones. EMBO J. 15:3792-3805.

43. Soto, G. E., S. J. Hultgren. 1999. Bacterial adhesins: common themes and variations in architecture and assembly. J. Bact. 181:1059-1071.

44. Zavialov, A. V., J. Berglund, A. F. Pudney, et al., 2003. Structure and biogenesis of the capsular F1 antigen from *Yersinia pestis*: preserved folding energy drives fiber formation. Cell 113:587-596.

Having described the invention, one of skill in the art will appreciate in the appended claims that many modifications and variations of the present invention are possible in light of the above teachings. It is therefore, to be understood that, within the scope of the appended claims, the invention may be practiced otherwise than as specifically described.

What is claimed is:

1. An immunogenic composition wherein said composition comprises a complex consisting of a whole or an antigenic polypeptide fragment of *Escherichia coli* fimbrial adhesin linked at the C-terminal end of said fimbrial adhesin to a linker which is operatively linked at the C-terminus of said linker to a whole or an antigenic polypeptide fragment of *Escherichia coli* major structural fimbrial subunit, wherein said whole or an antigenic polypeptide fragment of *Escherichia coli* fimbrial adhesin and whole or an antigenic polypeptide fragment of *Escherichia coli* major structural fimbrial subunit are derived from class 5 fimbriae.

2. The immunogenic composition of claim 1, wherein said whole or an antigenic polypeptide fragment of *Escherichia coli* fimbrial adhesin is a monomer or polymer of adhesin polypeptides.

3. The immunogenic composition of claim 1, wherein said whole or an antigenic polypeptide fragment of *Escherichia coli* fimbrial adhesin is selected from the group consisting of CfaE, CsfD, CsuD, CooD, CosD, CsdD, CsbD and CotD.

4. The immunogenic composition of claim 1, wherein said linker is composed of the amino acid sequence of SEQ ID No. 1, SEQ ID No. 2 or SEQ ID No. 3 or operable fragments thereof.

5. The immunogenic composition of claim 1, wherein said whole or an antigenic polypeptide fragment of *Escherichia coli* major structural fimbrial subunit is selected from the group consisting of CfaB, CsfA, CsuA1, CsuA2, CooA, CosA, CsbA, CsdA, and CotA.

6. The immunogenic composition of claim 5, wherein said polypeptide fragment is selected from the group consisting of SEQ ID No. 7, SEQ ID No. 8, SEQ ID No. 9, SEQ ID No. 10, SEQ ID No. 11, SEQ ID No. 12, SEQ ID No. 13, SEQ ID No. 14 and SEQ ID No. 15.

7. The immunogenic composition of claim 1, wherein said whole or an antigenic polypeptide fragment of *Escherichia coli* fimbriae major structural subunit confers conformational stability and protease resistance to said whole or an antigenic polypeptide fragment of *Escherichia coli* fimbrial adhesin.

8. The immunogenic composition of claim 1, wherein said whole or an antigenic polypeptide fragment of *Escherichia coli* fimbriae major structural fimbrial subunit is CfaB with SEQ ID No. 5 or SEQ ID No. 6 or antigenic fragment thereof.

9. A method of inducing an immune response comprising the steps:
   a. administering said immunogenic composition as in claim 1 at a unit dose range of 50 µg to 1 mg;
   b. administering a boosting dose of said immunogenic composition at least 1 week after priming dose with unit dose range of 50 µs to 1 mg in a buffered aqueous solution, wherein an immune response is elicited.

10. The method of claim 9, wherein said immune response is induced production of immunoglobulin molecules capable of binding to whole or an antigenic polypeptide fragment of *Escherichia coli* fimbriae.

11. The method of claim 9, wherein said immune response inhibits *Escherichia coli* adherence to human cells.

12. The method of claim 9, wherein said human cells are mucosal epithelial cells.

13. The method of claim 9, wherein said immunogenic composition is administered subcutaneously, transdermally, intramuscularly, orally, transcutaneously or nasally.

14. The method of claim 9, wherein said immune response reduces diarrhea in humans.

15. The method of claim 9, wherein said immune response inhibits adherence of diarrheagenic bacteria to human cells.

16. The method of claim 9, wherein said immune response reduces colonization of diarrheagenic bacteria.

17. A method of inducing an immune response comprising the steps:
   a. administering a priming dose of an immunogen containing a host bacterial cell containing said immunogenic composition as in claim 1 such that the expressed recombinant adhesin polypeptide of said immunogenic composition is 50 µg to 1 mg per dose; and
   b. administering 1 to 4 boosting doses of said host bacterial cell containing said immunogenic composition as in claim 1 with the first boosting dose at least 1 week after priming dose of said immunogen such that the expressed recombinant adhesin polypeptide of said immunogenic composition is 50 µg to 1 mg per dose, wherein an immune response is elicited.

18. The method of claim 17, wherein said host bacterial cell is a killed or live attenuated bacteria.

19. The method of claim 18, wherein said host bacterial cell is selected from the group consisting of *Escherichia coli*, member of the genus *Shigella*, member of the genus *Campylobacter*, member of the genus *Salmonella*, member of the genus *Vibrio*.

20. The method of claim 17, wherein said immune response is induction of immunoglobulin molecules capable of binding to said *Escherichia coli* fimbriae.

21. The method of claim 17, wherein said immune response inhibits *Escherichia coli* fimbriae adherence to human cells.

22. The method of claim 17, wherein said immune response inhibits *Escherichia coli* colonization to human cells.

23. The method of claim 21 wherein said human cells are mucosal epithelial cells.

24. The method of claim 17, wherein said immunogen is administered orally.

25. An immunogenic composition wherein said composition comprises a complex consisting of a whole or an antigenic polypeptide fragment of *Escherichia coli* coli surface antigen 3 ("CS3") linked at the C-terminal end of said CS3 to a linker which is operatively linked at the C-terminus of said linker to a donor strand polypeptide of CS3.

26. The immunogenic composition of claim 25, wherein said linker is composed of the amino acid sequence of SEQ ID No. 3.

27. The immunogenic composition of claim 25, wherein said complex comprising an amino acid sequence is SEQ ID No. 22.

28. The immunogenic composition of claim 25, wherein said complex comprising an amino acid sequence is SEQ ID No. 21.

29. A method of inducing an immune response comprising the steps:
   a. administering a priming dose of an immunogen containing a host bacterial cell containing said immunogenic composition as in claim 25 such that the expressed recombinant adhesin polypeptide of said immunogenic composition is 50 µg to 1 mg per dose; and
   b. administering 1 to 4 boosting doses of said host bacterial cell containing said immunogenic composition as in claim 25 with the first boosting dose at least 1 week after priming dose of said immunogen such that the expressed recombinant adhesin polypeptide of said immunogenic composition is 50 µg to 1 mg per dose, wherein an immune response is elicited.

30. The method of claim 29, wherein said host bacterial cell is a killed or live attenuated bacteria.

31. The method of claim 29, wherein said host bacterial cell is selected from the group consisting of *Escherichia coli*, member of the genus *Shigella*, member of the genus *Campylobacter*, member of the genus *Salmonella*, member of the genus *Vibrio*.

32. The method of claim 29, wherein said immune response is induction of immunoglobulin molecules capable of binding to said *Escherichia coli* fimbriae.

33. The method of claim 29, wherein said immune response inhibits *Escherichia coli* fimbriae adherence to human cells.

34. The method of claim 29, wherein said immune response inhibits *Escherichia coli* colonization to human cells.

35. The method of claim 33, wherein said human cells are mucosal epithelial cells.

36. The method of claim 29, wherein said immunogen is administered orally.

37. The immunogenic composition of claim 1, wherein said whole or an antigenic polypeptide fragment of *Escherichia coli* fimbrial adhesin is from *Escherichia coli* fimbriae selected from the group consisting of colonization factor antigen I, CS4, CS14, CSI, PCF071, CS17, CS19 and CS2.

38. The immunogenic composition of claim 25, wherein the whole or antigenic polypeptide fragment of *Escherichia coli* CS3 and the donor strand polypeptide of CS3 are both CstH.

39. The immunogenic composition of claim 38, wherein said CstH is composed of SEQ ID No. 23 or antigenic polypeptide fragments thereof.

\* \* \* \* \*

SEQUENCE LISTING

```
<160> NUMBER OF SEQ ID NOS: 28

<210> SEQ ID NO 1
<211> LENGTH: 4
<212> TYPE: PRT
<213> ORGANISM: Escherichia coli

<400> SEQUENCE: 1

Asp Asn Lys Gln
```

1

<210> SEQ ID NO 2
<211> LENGTH: 5
<212> TYPE: PRT
<213> ORGANISM: Escherichia coli

<400> SEQUENCE: 2

Gly Asp Asn Lys Gln
1               5

<210> SEQ ID NO 3
<211> LENGTH: 6
<212> TYPE: PRT
<213> ORGANISM: Escherichia coli

<400> SEQUENCE: 3

Gly Asp Asn Lys Gln Gly
1               5

<210> SEQ ID NO 4
<211> LENGTH: 360
<212> TYPE: PRT
<213> ORGANISM: Escherichia coli

<400> SEQUENCE: 4

Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

```
Asp Asn Ser Lys Ser Asp Gly Lys Phe Tyr Leu Lys Ile Asn Asp
            260                 265                 270

Asp Ser Lys Glu Leu Val Tyr Thr Leu Ser Leu Leu Ala Gly Lys
            275                 280                 285

Asn Leu Thr Pro Thr Asn Gly Gln Ala Leu Asn Ile Asn Thr Ala Ser
            290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                    325                 330                 335

Val Lys Asn Pro Glu Ala Gly Gln Tyr Met Gly Asn Ile Lys Ile Thr
            340                 345                 350

Phe Thr Pro Ser Ser Gln Thr Leu
            355                 360

<210> SEQ ID NO 5
<211> LENGTH: 170
<212> TYPE: PRT
<213> ORGANISM: Escherichia coli

<400> SEQUENCE: 5

Met Lys Phe Lys Lys Thr Ile Gly Ala Met Ala Leu Thr Thr Met Phe
1               5                   10                  15

Val Ala Val Ser Ala Ser Ala Val Glu Lys Asn Ile Thr Val Thr Ala
                20                  25                  30

Ser Val Asp Pro Ala Ile Asp Leu Leu Gln Ala Asp Gly Asn Ala Leu
            35                  40                  45

Pro Ser Ala Val Lys Leu Ala Tyr Ser Pro Ala Ser Lys Thr Phe Glu
        50                  55                  60

Ser Tyr Arg Val Met Thr Gln Val His Thr Asn Asp Ala Thr Lys Lys
65                  70                  75                  80

Val Ile Val Lys Leu Ala Asp Thr Pro Gln Leu Thr Asp Val Leu Asn
                85                  90                  95

Ser Thr Val Gln Met Pro Ile Ser Val Ser Trp Gly Gly Gln Val Leu
            100                 105                 110

Ser Thr Thr Ala Lys Glu Phe Glu Ala Ala Ala Leu Gly Tyr Ser Ala
        115                 120                 125

Ser Gly Val Asn Gly Val Ser Ser Gln Glu Leu Val Ile Ser Ala
    130                 135                 140

Ala Pro Lys Thr Ala Gly Thr Ala Pro Thr Ala Gly Asn Tyr Ser Gly
145                 150                 155                 160

Val Val Ser Leu Val Met Thr Leu Gly Ser
                165                 170

<210> SEQ ID NO 6
<211> LENGTH: 170
<212> TYPE: PRT
<213> ORGANISM: Escherichia coli

<400> SEQUENCE: 6

Met Lys Phe Lys Lys Thr Ile Gly Ala Met Ala Leu Thr Thr Met Phe
1               5                   10                  15

Val Ala Val Ser Ala Ser Ala Val Glu Lys Asn Ile Thr Val Thr Ala
                20                  25                  30

Ser Val Asp Pro Val Ile Asp Leu Leu Gln Ala Asp Gly Asn Ala Leu
            35                  40                  45
```

```
Pro Ser Ala Val Lys Leu Ala Tyr Ser Pro Ala Ser Lys Thr Phe Glu
    50                  55                  60

Ser Tyr Arg Val Met Thr Gln Val His Thr Asn Asp Ala Thr Lys Lys
65                  70                  75                  80

Val Ile Val Lys Leu Ala Asp Thr Pro Gln Leu Thr Asp Val Leu Asn
                85                  90                  95

Ser Thr Val Gln Met Pro Ile Ser Val Ser Trp Gly Gly Gln Val Leu
                100                 105                 110

Ser Thr Thr Ala Lys Glu Phe Glu Ala Ala Ala Leu Gly Tyr Ser Ala
            115                 120                 125

Ser Gly Val Asn Gly Val Ser Ser Ser Gln Glu Leu Val Ile Ser Ala
        130                 135                 140

Ala Pro Lys Thr Ala Gly Thr Ala Pro Thr Ala Gly Asn Tyr Ser Gly
145                 150                 155                 160

Val Val Ser Leu Val Met Thr Leu Gly Ser
                165                 170

<210> SEQ ID NO 7
<211> LENGTH: 20
<212> TYPE: PRT
<213> ORGANISM: Escherichia coli

<400> SEQUENCE: 7

Val Glu Lys Asn Ile Thr Val Thr Ala Ser Val Asp Pro Val Ile Asp
1               5                   10                  15

Leu Leu Gln Ala
            20

<210> SEQ ID NO 8
<211> LENGTH: 20
<212> TYPE: PRT
<213> ORGANISM: Escherichia coli

<400> SEQUENCE: 8

Val Glu Lys Asn Ile Thr Val Thr Ala Ser Val Asp Pro Thr Ile Asp
1               5                   10                  15

Ile Leu Gln Ala
            20

<210> SEQ ID NO 9
<211> LENGTH: 20
<212> TYPE: PRT
<213> ORGANISM: Escherichia coli

<400> SEQUENCE: 9

Val Glu Lys Asn Ile Thr Val Thr Ala Ser Val Asp Pro Thr Ile Asp
1               5                   10                  15

Ile Leu Gln Ala
            20

<210> SEQ ID NO 10
<211> LENGTH: 20
<212> TYPE: PRT
<213> ORGANISM: Escherichia coli

<400> SEQUENCE: 10

Val Glu Lys Asn Ile Thr Val Thr Ala Ser Val Asp Pro Thr Ile Asp
1               5                   10                  15

Ile Leu Gln Ala
```

-continued

```
            20

<210> SEQ ID NO 11
<211> LENGTH: 20
<212> TYPE: PRT
<213> ORGANISM: Escherichia coli

<400> SEQUENCE: 11

Val Glu Lys Thr Ile Ser Val Thr Ala Ser Val Asp Pro Thr Val Asp
1               5                   10                  15

Leu Leu Gln Ser
            20

<210> SEQ ID NO 12
<211> LENGTH: 20
<212> TYPE: PRT
<213> ORGANISM: Escherichia coli

<400> SEQUENCE: 12

Val Glu Lys Asn Ile Thr Val Arg Ala Ser Val Asp Pro Lys Leu Asp
1               5                   10                  15

Leu Leu Gln Ala
            20

<210> SEQ ID NO 13
<211> LENGTH: 20
<212> TYPE: PRT
<213> ORGANISM: Escherichia coli

<400> SEQUENCE: 13

Val Glu Lys Asn Ile Thr Val Arg Ala Ser Val Asp Pro Lys Leu Asp
1               5                   10                  15

Leu Leu Gln Ala
            20

<210> SEQ ID NO 14
<211> LENGTH: 20
<212> TYPE: PRT
<213> ORGANISM: Escherichia coli

<400> SEQUENCE: 14

Ala Glu Lys Asn Ile Thr Val Thr Ala Ser Val Asp Pro Thr Ile Asp
1               5                   10                  15

Leu Met Gln Ser
            20

<210> SEQ ID NO 15
<211> LENGTH: 20
<212> TYPE: PRT
<213> ORGANISM: Escherichia coli

<400> SEQUENCE: 15

Val Glu Lys Thr Ile Ser Val Thr Ala Ser Val Asp Pro Thr Val Asp
1               5                   10                  15

Leu Leu Gln Ser
            20

<210> SEQ ID NO 16
<211> LENGTH: 57
<212> TYPE: DNA
<213> ORGANISM: Escherichia coli

<400> SEQUENCE: 16
```
tcgacaataa acaagtagag aaaaatatta ctgtaacagc tagtgttgat ccttagc    57

<210> SEQ ID NO 17
<211> LENGTH: 57
<212> TYPE: DNA
<213> ORGANISM: Escherichia coli

<400> SEQUENCE: 17
tcgagctaag gatcaacact agctgttaca gtaatatttt tctctacttg tttattg    57

<210> SEQ ID NO 18
<211> LENGTH: 20
<212> TYPE: PRT
<213> ORGANISM: Escherichia coli

<400> SEQUENCE: 18

Asp Lys Asn Pro Gly Ser Glu Asn Met Thr Asn Thr Ile Gly Pro His
1               5                   10                  15

Asp Arg Gly Gly
            20

<210> SEQ ID NO 19
<211> LENGTH: 168
<212> TYPE: PRT
<213> ORGANISM: Escherichia coli

<400> SEQUENCE: 19

Met Leu Lys Ile Lys Tyr Leu Leu Ile Gly Leu Ser Leu Ser Ala Met
1               5                   10                  15

Ser Ser Tyr Ser Leu Ala Ala Ala Gly Pro Thr Leu Thr Lys Glu Leu
                20                  25                  30

Ala Leu Asn Val Leu Ser Pro Ala Ala Leu Asp Ala Thr Trp Ala Pro
            35                  40                  45

Gln Asp Asn Leu Thr Leu Ser Asn Thr Gly Val Ser Asn Thr Leu Val
        50                  55                  60

Gly Val Leu Thr Leu Ser Asn Thr Ser Ile Asp Thr Val Ser Ile Ala
65                  70                  75                  80

Ser Thr Asn Val Ser Asp Thr Ser Lys Asn Gly Thr Val Thr Phe Ala
                85                  90                  95

His Glu Thr Asn Asn Ser Ala Ser Phe Ala Thr Thr Ile Ser Thr Asp
            100                 105                 110

Asn Ala Asn Ile Thr Leu Asp Lys Asn Ala Gly Asn Thr Ile Val Lys
        115                 120                 125

Thr Thr Asn Gly Ser Gln Leu Pro Thr Asn Leu Pro Leu Lys Phe Ile
    130                 135                 140

Thr Thr Glu Gly Asn Glu His Leu Val Ser Gly Asn Tyr Arg Ala Asn
145                 150                 155                 160

Ile Thr Ile Thr Ser Thr Ile Lys
                165

<210> SEQ ID NO 20
<211> LENGTH: 16
<212> TYPE: PRT
<213> ORGANISM: Escherichia coli

<400> SEQUENCE: 20

Ala Ala Gly Pro Thr Leu Thr Lys Glu Leu Ala Leu Asn Val Leu Ser
1               5                   10                  15

<210> SEQ ID NO 21
<211> LENGTH: 190
<212> TYPE: PRT
<213> ORGANISM: Escherichia coli

<400> SEQUENCE: 21

Met Gly His His His His His His His His Ser Ser Gly His
1               5                   10                  15

Ile Asp Asp Asp Lys His Met Ala Ala Gly Pro Thr Leu Thr Lys
                20                  25                  30

Glu Leu Ala Leu Asn Val Leu Ser Pro Ala Ala Leu Asp Ala Thr Trp
            35                  40                  45

Ala Pro Gln Asp Asn Leu Thr Leu Ser Asn Thr Gly Val Ser Asn Thr
        50                  55                  60

Leu Val Gly Val Leu Thr Leu Ser Asn Thr Ser Ile Asp Thr Val Ser
65                  70                  75                  80

Ile Ala Ser Thr Asn Val Ser Asp Thr Ser Lys Asn Gly Thr Val Thr
                85                  90                  95

Phe Ala His Glu Thr Asn Asn Ser Ala Ser Phe Ala Thr Thr Ile Ser
            100                 105                 110

Thr Asp Asn Ala Asn Ile Thr Leu Asp Lys Asn Ala Gly Asn Thr Ile
        115                 120                 125

Val Lys Thr Thr Asn Gly Ser Gln Leu Pro Thr Asn Leu Pro Leu Lys
    130                 135                 140

Phe Ile Thr Thr Glu Gly Asn Glu His Leu Val Ser Gly Asn Tyr Arg
145                 150                 155                 160

Ala Asn Ile Thr Ile Thr Ser Thr Ile Lys Asp Asn Lys Gln Ala Ala
                165                 170                 175

Gly Pro Thr Leu Thr Lys Glu Leu Ala Leu Asn Val Leu Ser
            180                 185                 190

<210> SEQ ID NO 22
<211> LENGTH: 175
<212> TYPE: PRT
<213> ORGANISM: Escherichia coli

<400> SEQUENCE: 22

Met Ala Ala Gly Pro Thr Leu Thr Lys Glu Leu Ala Leu Asn Val Leu
1               5                   10                  15

Ser Pro Ala Ala Leu Asp Ala Thr Trp Ala Pro Gln Asp Asn Leu Thr
                20                  25                  30

Leu Ser Asn Thr Gly Val Ser Asn Thr Leu Val Gly Val Leu Thr Leu
            35                  40                  45

Ser Asn Thr Ser Ile Asp Thr Val Ser Ile Ala Ser Thr Asn Val Ser
        50                  55                  60

Asp Thr Ser Lys Asn Gly Thr Val Thr Phe Ala His Glu Thr Asn Asn
65                  70                  75                  80

Ser Ala Ser Phe Ala Thr Thr Ile Ser Thr Asp Asn Ala Asn Ile Thr
                85                  90                  95

Leu Asp Lys Asn Ala Gly Asn Thr Ile Val Lys Thr Thr Asn Gly Ser
            100                 105                 110

Gln Leu Pro Thr Asn Leu Pro Leu Lys Phe Ile Thr Thr Glu Gly Asn
        115                 120                 125

Glu His Leu Val Ser Gly Asn Tyr Arg Ala Asn Ile Thr Ile Thr Ser
    130                 135                 140

Thr Ile Lys Asp Asn Lys Gln Ala Ala Gly Pro Thr Leu Thr Lys Glu
145                 150                 155                 160

Leu Ala Leu Asn Val Leu Ser Leu Glu His His His His His His
                165                 170                 175

<210> SEQ ID NO 23
<211> LENGTH: 146
<212> TYPE: PRT
<213> ORGANISM: Escherichia coli

<400> SEQUENCE: 23

Ala Ala Gly Pro Thr Leu Thr Lys Glu Leu Ala Leu Asn Val Leu Ser
1               5                   10                  15

Pro Ala Ala Leu Asp Ala Thr Trp Ala Pro Gln Asp Asn Leu Thr Leu
                20                  25                  30

Ser Asn Thr Gly Val Ser Asn Thr Leu Val Gly Val Leu Thr Leu Ser
            35                  40                  45

Asn Thr Ser Ile Asp Thr Val Ser Ile Ala Ser Thr Asn Val Ser Asp
        50                  55                  60

Thr Ser Lys Asn Gly Thr Val Thr Phe Ala His Glu Thr Asn Asn Ser
65                  70                  75                  80

Ala Ser Phe Ala Thr Thr Ile Ser Thr Asp Asn Ala Asn Ile Thr Leu
                85                  90                  95

Asp Lys Asn Ala Gly Asn Thr Ile Val Lys Thr Thr Asn Gly Ser Gln
                100                 105                 110

Leu Pro Thr Asn Leu Pro Leu Lys Phe Ile Thr Thr Glu Gly Asn Glu
            115                 120                 125

His Leu Val Ser Gly Asn Tyr Arg Ala Asn Ile Thr Ile Thr Ser Thr
        130                 135                 140

Ile Lys
145

<210> SEQ ID NO 24
<211> LENGTH: 20
<212> TYPE: PRT
<213> ORGANISM: Escherichia coli

<400> SEQUENCE: 24

Val Gln Lys Asp Ile Thr Val Thr Ala Asn Val Asp Thr Thr Leu Glu
1               5                   10                  15

Met Leu Ser Ala
            20

<210> SEQ ID NO 25
<211> LENGTH: 20
<212> TYPE: PRT
<213> ORGANISM: Escherichia coli

<400> SEQUENCE: 25

Val Gln Lys Asp Ile Thr Val Thr Ala Asn Ile Asp Ser Thr Leu Glu
1               5                   10                  15

Leu Leu Gln Ala
            20

<210> SEQ ID NO 26
<211> LENGTH: 20
<212> TYPE: PRT
<213> ORGANISM: Artificial Sequence
<220> FEATURE:
<223> OTHER INFORMATION: Common motif

```
<220> FEATURE:
<221> NAME/KEY: MISC_FEATURE
<222> LOCATION: (1)..(1)
<223> OTHER INFORMATION: Xaa is a hydrophobic residue.
<220> FEATURE:
<221> NAME/KEY: MISC_FEATURE
<222> LOCATION: (2)..(2)
<223> OTHER INFORMATION: Xaa is Gln or Glu.
<220> FEATURE:
<221> NAME/KEY: MISC_FEATURE
<222> LOCATION: (4)..(4)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.
<220> FEATURE:
<221> NAME/KEY: MISC_FEATURE
<222> LOCATION: (5)..(5)
<223> OTHER INFORMATION: Xaa is a hydrophobic residue.
<220> FEATURE:
<221> NAME/KEY: MISC_FEATURE
<222> LOCATION: (7)..(7)
<223> OTHER INFORMATION: Xaa is a hydrophobic residue.
<220> FEATURE:
<221> NAME/KEY: MISC_FEATURE
<222> LOCATION: (8)..(8)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.
<220> FEATURE:
<221> NAME/KEY: MISC_FEATURE
<222> LOCATION: (10)..(10)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.
<220> FEATURE:
<221> NAME/KEY: MISC_FEATURE
<222> LOCATION: (11)..(11)
<223> OTHER INFORMATION: Xaa is a hydrophobic residue.
<220> FEATURE:
<221> NAME/KEY: MISC_FEATURE
<222> LOCATION: (13)..(13)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.
<220> FEATURE:
<221> NAME/KEY: MISC_FEATURE
<222> LOCATION: (14)..(14)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.
<220> FEATURE:
<221> NAME/KEY: MISC_FEATURE
<222> LOCATION: (15)..(15)
<223> OTHER INFORMATION: Xaa is a hydrophobic residue.
<220> FEATURE:
<221> NAME/KEY: MISC_FEATURE
<222> LOCATION: (17)..(17)
<223> OTHER INFORMATION: Xaa is a hydrophobic residue.
<220> FEATURE:
<221> NAME/KEY: MISC_FEATURE
<222> LOCATION: (18)..(18)
<223> OTHER INFORMATION: Xaa is a hydrophobic residue.
<220> FEATURE:
<221> NAME/KEY: MISC_FEATURE
<222> LOCATION: (19)..(19)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.
<220> FEATURE:
<221> NAME/KEY: MISC_FEATURE
<222> LOCATION: (20)..(20)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.

<400> SEQUENCE: 26

Xaa Xaa Lys Xaa Xaa Thr Xaa Xaa Ala Xaa Xaa Asp Xaa Xaa Xaa Asp
1               5                   10                  15

Xaa Xaa Xaa Xaa
            20

<210> SEQ ID NO 27
<211> LENGTH: 19
```

```
<212> TYPE: PRT
<213> ORGANISM: Artificial Sequence
<220> FEATURE:
<223> OTHER INFORMATION: Common motif
<220> FEATURE:
<221> NAME/KEY: MISC_FEATURE
<222> LOCATION: (3)..(3)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.
<220> FEATURE:
<221> NAME/KEY: MISC_FEATURE
<222> LOCATION: (5)..(5)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.
<220> FEATURE:
<221> NAME/KEY: MISC_FEATURE
<222> LOCATION: (7)..(7)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.
<220> FEATURE:
<221> NAME/KEY: MISC_FEATURE
<222> LOCATION: (8)..(8)
<223> OTHER INFORMATION: Xaa is a hydrophobic residue.
<220> FEATURE:
<221> NAME/KEY: MISC_FEATURE
<222> LOCATION: (9)..(9)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.
<220> FEATURE:
<221> NAME/KEY: MISC_FEATURE
<222> LOCATION: (10)..(10)
<223> OTHER INFORMATION: Xaa is a hydrophobic residue.
<220> FEATURE:
<221> NAME/KEY: MISC_FEATURE
<222> LOCATION: (11)..(11)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.
<220> FEATURE:
<221> NAME/KEY: MISC_FEATURE
<222> LOCATION: (12)..(12)
<223> OTHER INFORMATION: Xaa is a hydrophobic residue.
<220> FEATURE:
<221> NAME/KEY: MISC_FEATURE
<222> LOCATION: (14)..(19)
<223> OTHER INFORMATION: Xaa is Gly, Pro, Ala, Val, Leu, Ile, Met, Cys,
      Phe, Tyr, Trp, His, Lys, Arg, Gln, Asn, Glu, Asp, Ser, or Thr.

<400> SEQUENCE: 27

Ala Gly Xaa Tyr Xaa Gly Xaa Xaa Xaa Xaa Xaa Xaa Thr Xaa Xaa Xaa
1               5                   10                  15

Xaa Xaa Xaa

<210> SEQ ID NO 28
<211> LENGTH: 10
<212> TYPE: PRT
<213> ORGANISM: Escherichia coli

<400> SEQUENCE: 28

Val Glu Lys Asn Ile Thr Val Thr Ala Ser
1               5                   10
```